US008237017B2

(12) United States Patent
Bots et al.

(10) Patent No.: US 8,237,017 B2
(45) Date of Patent: Aug. 7, 2012

(54) STRESS-RELATED MICRORNA MOLECULES AND USES THEREOF

(75) Inventors: Marc Bots, Ghent (BE); Michael Metzlaff, Tervuren (BE)

(73) Assignee: Bayer CropScience NV, Diegem (BE)

( * ) Notice: Subject to any disclaimer, the term of this patent is extended or adjusted under 35 U.S.C. 154(b) by 408 days.

(21) Appl. No.: 12/300,386

(22) PCT Filed: May 10, 2007

(86) PCT No.: PCT/EP2007/004142
§ 371 (c)(1),
(2), (4) Date: Dec. 15, 2008

(87) PCT Pub. No.: WO2007/131699
PCT Pub. Date: Nov. 22, 2007

(65) Prior Publication Data
US 2009/0151021 A1  Jun. 11, 2009

Related U.S. Application Data

(60) Provisional application No. 60/808,036, filed on May 24, 2006.

(30) Foreign Application Priority Data

May 12, 2006 (EP) .................................... 06009836

(51) Int. Cl.
*A01H 5/00* (2006.01)
*C12N 15/82* (2006.01)
*C12N 15/63* (2006.01)
*C12N 5/14* (2006.01)
(52) U.S. Cl. ..................... 800/298; 800/285; 435/320.1; 435/419
(58) Field of Classification Search .................. None
See application file for complete search history.

(56) References Cited

U.S. PATENT DOCUMENTS

| 7,723,568 B2 * | 5/2010 | Lutfiyya et al. ............... 800/285 |
| 2005/0144669 A1 | 6/2005 | Reinhart et al. |
| 2005/0166289 A1 * | 7/2005 | Chuan Chiang et al. ..... 800/286 |

FOREIGN PATENT DOCUMENTS

| WO | WO 89/03887 | 5/1989 |
| WO | WO 89/10396 | 11/1989 |
| WO | WO 92/13956 | 8/1992 |
| WO | WO 96/06932 | 3/1996 |
| WO | WO 97/13865 | 4/1997 |
| WO | WO 99/37789 A | 7/1999 |
| WO | WO 00/04173 A | 1/2000 |
| WO | WO 00/63397 | 10/2000 |
| WO | WO 02/13964 | 2/2002 |
| WO | WO 03/029459 | 4/2003 |
| WO | WO 2004/009779 | 1/2004 |
| WO | WO 2004/090140 A | 10/2004 |
| WO | WO 2005/017111 | 2/2005 |
| WO | WO 2005/035769 | 4/2005 |
| WO | WO 2005/047505 | 5/2005 |
| WO | WO 2005/052170 | 6/2005 |
| WO | WO 2005/078096 | 8/2005 |
| WO | WO 2005/100574 | 10/2005 |
| WO | WO 2006/044322 | 4/2006 |
| WO | WO 2006/045633 A | 5/2006 |
| WO | WO 2006/133827 A | 12/2006 |

OTHER PUBLICATIONS

Bartel et al., Cell, 2004, vol. 116, pp. 281-297.*
Perriman et al., PNAS, 1995, vol. 92, pp. 6175-6179.*
Jones-Rhoades et al. (Molecular Cell, 14:787-799, 2004).*
Parizotto, et al. (2004) Genes and Development 18: 2237-2242.
Accession No. AL764433 "*Arabidopsis thaliana* T-DNA flanking sequence GK-125G09-012923." (Jun. 18, 2002).
Accession No. AF159377 "*Arabidopsis thaliana* phosphomannose isomerase (din9) mRNA, partial cds." (Oct. 17, 2000).
Accession No. AL764435 "*Arabidopsis thaliana* T-DNA flanking sequence GK-125G10-012923." (Jun. 18, 2002).
Alvarez, et al. (2006) Plant Cell 18(5) : 1134-1151.
An, et al. (1996) Plant Journal 10: 107-121.
Amor, et al. (Nov. 27, 1998) "The involvement of poly(ADP-ribose) polymerase in the oxidative stress responses in plants." FEBS Letter 440(1-2): 1-7.
Barb, et al. (Sep. 2003) "A *Nicotiana tabacum* cell culture selected for accelerated growth on mannose has increased expression of phosphomannose isomerase." Plant Science 165(3): 639-648.
Borsani, et al. (Dec. 2005) "Endogenous siRNAs derived from a pair of natural cis-antisense transcripts regulate salt tolerance in *Arabidopsis*." Cell 123(7): 1279-1291.
Chiou, et al. (Feb. 2006) "Regulation of phosphate homeostasis by microRNA in *Arabidopsis*." Plant Cell 18(2): 412-421.
De Block, et al. (Jan. 2005) "Poly(ADP-ribose) polymerase in plants affects energy homeostasis, cell death and stress tolerance." Plant Journal 41(1): 95-106.
Doucet-Chabeaud, et al. (Aug. 2001) "Ionising radiation induces the expression of PARP-1 and PARP-2 genes in *Arabidopsis*." Molecular Genetics and Genomics 265(6): 954-963.
Fujii, et al. (Nov. 22, 2005) "A miRNA involved in Phosphate-Starvation Response in *Arabidopsis*." Current Biology 15(22): 2038-2043.
Fukiki, et al. (Mar. 2001) "Dark-inducible genes from *Arabidopsis thaliana* are associated with leaf senescence and repressed by sugars." Physiologia Plantarum 111(3): 345-352.
Han, et al. (2006) Cell 125: 887-901.
Harpster, et al. (1988) Mol. Gen. Genet. 212: 182-190.
Hudspeth, et al. (1989) Plant Mol Biol. 12: 579-589.
Jones-Rhoades, et al. (Jun. 18, 2004) "Computational identification of plant microRNAs and their targets, including a stress-induced miRNA." Molecular Cell 14(6): 787-799.
Kameoka, et al. (Aug. 2004) "RNA interference directed against poly(ADP-ribose) polymerase 1 efficiently suppresses human immunodeficiency virus type 1 replication in human cells." Journal of Virology 78(16): 8931-8934.
Keil, et al. (1989) EMBO J. 8(5): 1323-1330.
Keller, et al. (1988) EMBO J. 7: 3625-2633.
Keller, et al. (1989) Genes Devel. 3: 1639-1646.

(Continued)

Primary Examiner — Vinod Kumar
(74) Attorney, Agent, or Firm — Hunton & Williams LLP

(57) ABSTRACT

Naturally occurring and synthetic novel stress-related miRNAs are provided which can be used to modify the stress tolerance of plants.

6 Claims, 12 Drawing Sheets

OTHER PUBLICATIONS

Kusaba (Apr. 2004) "RNA interference in crop plants." Current Opinion in Biotechnology 15(2): 139-143.
Lu, et al. (Aug. 2005) "Novel and mechanical stress-responsive microRNAs in *Populus trichocarpa* that are absent from *Arabidopsis*." Plant Cell 17(8): 2186-2203.
Panda, et al. (2002) Dev. Cell. 3: 51-61.
Peleman, et al. (1989) Gene 84: 359-369.
Schwab, et al. (2005) Developmental Cell 8: 517-527.
Schwab, et al. (2006) Plant Cell 18(5): 1121-1133.
Sunkar, et al. (Aug. 2004) "Novel and stress-regulated microRNAs and other small RNAs from *Arabidopsis*." Plant Cell 16(8): 2001-2019.
Rosso, et al. (Sep. 2003) "An *Arabidopsis thaliana* T-DNA mutagenized population (GABI-Kat) for flanking sequence tag-based reverse genetics." Plant Molecular Biology 53(1-2): 247-259.
Zhang, et al. (Jan. 1, 2006) "Plant microRNA: A small regulatory molecule with big impact." Developmental Biology 289(1): 3-16.
Zucker, et al. (2003) Nucleic Acid Research 31: 3406-3415.

\* cited by examiner

A

PARP1     ugguuacauguuuggaaaagg
          ||||||||||||||||||||
miRPARP   accaauguacaaaccuuuucc

- No mismatches
- Free energy: -32.7 kcal/mol

B

PARP1     ugguuacauguuuggaaaagg
          ||:||||||||:|||||||
miRPARP2m acuaauguacaaaucuuuucc Free energy: -27.8 kcal/mol
(85% of perfect match)

C

PARP1     ugguuacauguuuggaaaagg
          ||:|||||||||:|||||||
miRPARP3m acucauguacaaaucuuuucc Free energy: -23.9 kcal/mol
(73% of perfect match)

Figure 2 miRPARP7: TAGACGATATACATTGTAC

Figure 3 pre-miR398a
(miRNA*, miRNA)

GTCTCCATGGGAACAACAGGAGGTGAAATT
TCAAAGGAGTGGCATGTGAACACATATCCT
ATGGTTTCTTCAAATTCCATTGAAACCAT
TGAGTTTTGTGTTCTCAGGTCACCCCTTTG
AATCTCCCCTGTTCCATTGCTAGCTCTG (SEQ ID NO: 39)

pre-miRPARP2-8
(miRNA*, miRNA)

GTCTCCATGGGAACAACAGGAGGTGAAATTT
CAGTACTATGTAAATTTCGTCTATATCCT
ATGGTTTCTTCAAATTCCATTGAAACCATT
GAGTTTTAGACGATATATACATTGTACTG
AATCTCCCCTGTTCCATTGCTAGCTCTG (SEQ ID NO: 40)

FIGURE 4

| target nr | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| AtPARP1 | C | A | T | C | A | G | C | T | G | A | G | T | T | G | C | G | G | G | A | A | A |
| AtPARP2 | C | G | T | G | A | G | G | A | A | G | C | T | A | T | T | A | A | G | A | G | A |
| miRPARP8 | G | C | G | C | T | C | C | T | T | C | G | | | A | A | T | A | C | T | C | T |
| miR nr | 21 | 20 | 19 | 18 | 17 | 16 | 15 | 14 | 13 | 12 | 11 | 10 | 9 | 8 | 7 | 6 | 5 | 4 | 3 | 2 | 1 | miRPARP8: TCTCATAATAGCTTCCTCGCG

Figure 5

```
GTCTCCATGGGAACAACAGGAGGTGAAATT            GTCTCCATGGGAACAACAGGAGGTGAAATT
TCAAAGGAGTGGCATGTGAACACATATCCT            TCACGCGTGGAAGATAATATGAGATATCCT
ATGGTTTCTTCAAATTCCATTGAAACCAT             ATGGTTTCTTCAAATTCCATTGAAACCAT
TGAGTTTTGTGTTCTCAGGTCACCCCTTTG  ⟹          TGAGTTTTCTCATAATAGCTTCCTCGCGTG
AATCTCCCCGTTCCATTGCTAGCTCTG               AATCTCCCCGTTCCATTGCTAGCTCTG pre-miR398a                               pre-miRPARP2-8
(miRNA*, miRNA)                           (miRNA*, miRNA)

(SEQ ID NO: 39)                           (SEQ ID NO: 42)
```

FIGURE 6

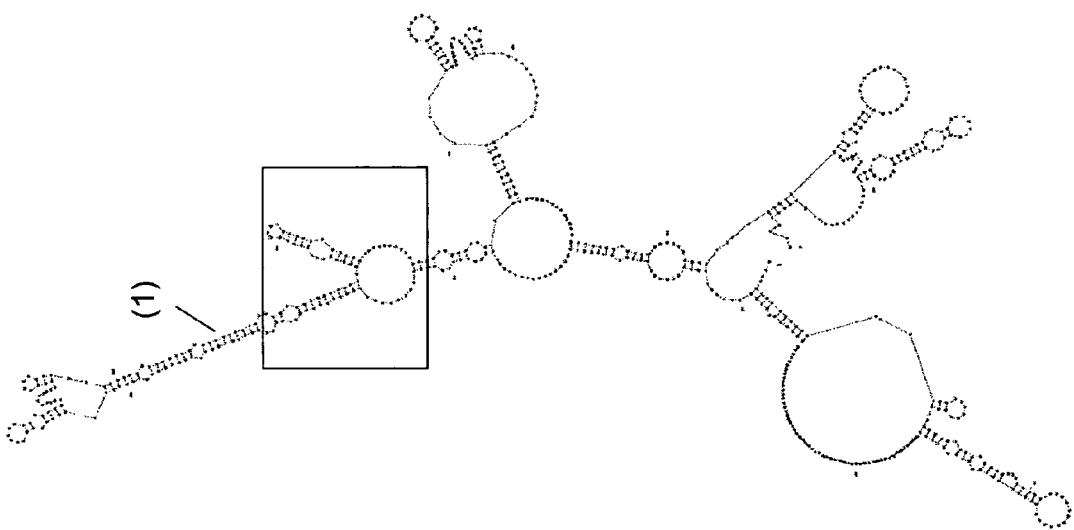
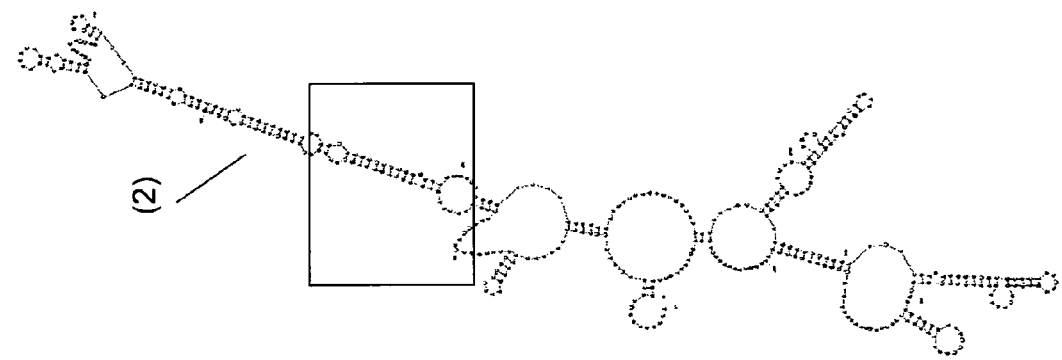
Figure 9

STRESS-RELATED MICRORNA MOLECULES AND USES THEREOF

CROSS-REFERENCE TO RELATED APPLICATIONS

This application is the U.S. National Stage filing of International Application No. PCT/EP2007/004142, filed May 10, 2007, which claims priority to EP 06009836.5, filed May 12, 2006 and U.S. Provisional Patent Application No. 60/808,036, filed May 24, 2006, the disclosures of each of which are hereby incorporated by reference.

FIELD OF THE INVENTION

The invention relates to the agricultural field, more particularly to the use of novel stress-related micro RNA molecules (miRNAs) to alter the tolerance of plants to adverse growing conditions and to modify the tolerance of plants to stress conditions, particularly abiotic stress conditions such as, but not limited to, low or high temperatures, drought, high light intensities, chemical pollution, flooding, high salinity, high light intensities, high UV irradiation and the like. Described novel miRNAs and precursors thereof and methods to use such miRNAs and precursors thereof increase or decrease the stress tolerance of plants. Also described are synthetic miRNAs to increase the stress tolerance of plants.

BACKGROUND ART

Short RNA molecules, of about 21 to 24 nucleotides in length, have been shown to be involved in the mechanism of post transcriptional gene silencing in eukaryotes. These molecules are generated through the cleavage of long double stranded RNA molecules by RNAse III enzymes (DICER in animals; DICERLIKE in plants) and are used as guide-sequences incorporated in a RISC complex for the sequence-specific degradation of the target RNA (mRNA) molecules. The short RNA molecules can also be recruited in silencing complexes which interfere in a sequence specific manner with target gene expression by specific chromatin remodeling and methylation.

Recently, a novel class of short RNA molecules was discovered in animals and plants and named microRNA (miRNA). MicroRNAs are small endogenous RNAs that regulate gene expression in plants, but also in other eukaryotes. In plants, these about 21 nucleotide long RNAs are processed from the stem-loop regions of long endogenous primary transcripts by the cleavage activity of DCL1. Plant miRNAs are highly complementary to conserved target mRNAs, and guide the cleavage of their targets. miRNAs appear to be key components in regulating the gene expression of complex networks of pathways involved i.a. in development.

In animals, the biogenesis of miRNA from the longer primary transcripts (pri-miRNA) involves two steps. First, the miRNA stem-loop (pre-miRNA) is liberated from the pri-miRNA in the nucleus by cleavage on each arm of the stem-loop, effected by Drosha. After export to the cytoplasm, DICER makes a second set of cuts separating the miRNA (duplexed with its near reverse complement microRNA*) from the loop region of the pre-miRNA. In plants, both steps are carried out by DCL1 and presumably both steps occur in the nucleus.

International patent application WO 03/029459 described 22 and 21 nucleotide RNAs that function as key regulators in developmental timing in *Caenorhabditis elegans*.

WO2004/009779 describes compositions and methods for modulating nucleotide sequence expression, particularly for modulating gene expression in plants. The compositions comprise precursor RNA constructs for the expression of an RNA precursor. The precursor RNA construct comprises a promoter that is expressed in a plant cell driving the expression of a precursor RNA having a microRNA. The miRNA is complementary or partially complementary to a portion of a target gene or nucleotide sequence and function to modulate expression of the target sequence or gene. In this manner, the RNA precursor construct can be designed to modulate expression of any nucleotide sequence of interest, either an endogenous plant gene or alternatively a transgene. The precursor RNA constructs may be used in combination with modulators to enhance the effect on gene expression. Expression of a modulator in the presence of the precursor RNA alters the accumulation of miRNAs and thus enhances the regulatory capabilities of miRNAs. The document further describes the use of a modulator to control gene expression via both siRNA and the miRNA pathway. Transformed plants, tissues, cells and seeds are also provided.

WO2005/017111 describes a method of identifying a microRNA-recognition element and of generating microRNAs as well as a system and computer programs for performing such methods. Recombinant nucleic acid molecule comprising a heterologous coding sequence and one or more MREs are also disclosed as are isolated nucleic acid molecule comprising one or more MRE sequences and being free of a coding sequence operably linked to regulatory elements. MicroRNA generated by a methods of the invention and the use of the microRNAs to downregulate gene expression are also described.

WO 2005/035769 and WO 2005/052170 provide methods and compositions useful in target sequence suppression and target sequence validation. The application also describes polynucleotide constructs useful for gene silencing, as well as cells, plants and seeds comprising the polynucleotides. Further provided is a method for using microRNA to silence a target sequence.

WO2005/047505 relates to microRNAs, methods of producing microRNAs and methods for using microRNAs.

WO 2005/078096 is based, in part, on the discovery that endogenous miRNAs can be recruited for translational repression of target mRNAs. The RNA-silencing agents and the methods described herein, provide a means by which to treat genetic (e.g., genetic neurodegenerative diseases such as Huntington's Disease) or non-genetic diseases by, for example, blocking the synthesis of proteins that contribute to the diseases. Accordingly the described RNA-silencing agents have an mRNA targeting moiety, a linking moiety, and a miRNA recruiting moiety.

WO2005/100574 relates to means and methods for modifying biomass yield and/or plant growth and/or plant architecture of plants. In particular, it concerns transgenic plants exhibiting an increased biomass yield and plant growth rate compared to the corresponding wild-type plants. These plants are characterized by containing altered levels of a microRNA, in particular microRNA that targets members of the SPL family of genes encoding SPL transcription factors.

WO2006/034368 describes miRNAs, particularly from poplars, for plant growth and development.

WO2006/044322 describes methods and compositions useful in target sequence suppression, target sequence validation and target sequence down regulation. The document provides polynucleotide constructs useful for gene silencing or RNA down regulation, as well as cells, plants and seeds comprising the polynucleotides. Also provided is a method for using microRNA to silence a target sequence or to down regulate RNA.

Abreu et al. (2004, Genes and Development 18:2237-2242) describe in vivo investigation of the transcription, processing, endonucleolytic activity and functional relevance of the spatial distribution of a plant miRNA. To this end a synthetic miRNA miR171 targeting the coding region for GFP was constructed.

Schwab et al. (2005, Developmental Cell, 8: 517-527) describe specific effects of miRNAs on the plant transcriptome and deduced a set of empirical parameters for target recognition which could be applied to synthetic miRNAs.

Schwab et al. (2006, Plant Cell, 18(5):1121-1133) described highly specific gene silencing by artificial miRNAs, targeted to reduce the expression of different genes, in *Arabidopsis*.

Alvarez et al 2006 (Plant Cell. 2006 May; 18(5):1134-1151) described that endogenous and synthetic microRNAs stimulate simultaneous, efficient and localized regulation of multiple targets in diverse species, including tobacco and tomato.

WO 00/04173 describes methods to modulate programmed cell death (PCD) in eukaryotic cells and organisms, particularly plant cells and plants, by introducing of "PCD modulating chimeric genes" influencing the expression and/or apparent activity of endogenous poly-(ADP-ribose) polymerase (PARP) genes. Programmed cell death may be inhibited or provoked. The invention particularly relates to the use of nucleotide sequences encoding proteins with PARP activity for modulating PCD, for enhancing growth rate or for producing stress tolerant cells and organisms.

WO 2004/090140 describes methods and means to increase the tolerance of plants to abiotic stress or adverse growing conditions, including drought, high light intensities, high temperatures, nutrient limitations and the like by reducing the activity of endogenous PARG proteins in plants.

WO2006/045633 describes the use of cotton parp2 gene or cDNA sequences to obtain stress tolerant cotton plants. Various cotton parp2 sequences are also provided.

None of the prior art documents describe miRNAs involved in the regulation of the response of plants to adverse abiotic conditions or the use thereof to modify the stress tolerance of plants. Neither do any of the prior art documents describe a synthetic miRNA which can be used to modify the stress tolerance of plants.

The aim of the current invention is to provide such stress-related miRNA molecules as well as synthetic miRNA molecules which can be used to modify or increase the tolerance of plants to adverse growing conditions and make them more resistant to stress conditions such as abiotic stress conditions.

SUMMARY OF THE INVENTION

In one embodiment, the invention provides isolated RNA molecules or DNA molecules comprising the nucleotide sequence of any one of SEQ ID No.: 1 to SEQ ID No. 36 or a variant thereof capable of guiding the cleavage of the same target sequences.

In another embodiment, the invention provides a chimeric gene comprising a plant-expressible promoter operably linked to a DNA region which upon introduction and transcription in a plant cell is processed into a miRNA, the DNA region comprising the nucleotide sequence of any one of SEQ ID No.: 1 to SEQ ID No. 36 or a variant thereof capable of guiding the cleavage of the same target sequences; and optionally, a 3' DNA region involved in transcription termination and polyadenylation. The plant-expressible promoter may be a constitutive promoter or a tissue specific promoter or an inducible promoter.

In yet another embodiment the invention provides a plant cell or a plant comprising a chimeric gene comprising a plant-expressible promoter operably linked to a DNA region which upon introduction and transcription in a plant cell is processed into a miRNA, the DNA region comprising the nucleotide sequence of any one of SEQ ID No.: 1 to SEQ ID No. 36 or a variant thereof capable of guiding the cleavage of the same target sequences; and optionally, a 3' DNA region involved in transcription termination and polyadenylation.

The invention also provides a method for increasing the resistance of plants to adverse growing conditions, comprising the steps of introducing a chimeric gene into cells of the plants, the chimeric gene comprising the following operably linked DNA regions: a plant expressible promoter; a DNA region which upon introduction and transcription in a plant cell is processed into a miRNA, the miRNA being capable of recognizing and guiding the cleavage of the mRNA of an endogenous PARP gene or ParG gene of the plant; and optionally, a 3' DNA region involved in transcription termination and polyadenylation.

Preferably, the mentioned miRNA encoding DNA region comprises a nucleotide sequence which is essentially complementary to a nucleotide sequence of at least 21 consecutive nucleotides of the endogenous PARP gene or ParG gene of the plant, provided that one or more of following mismatches are allowed: a mismatch between the nucleotide at the 5' end of the miRNA and the corresponding nucleotide sequence in the RNA molecule; a mismatch between any one of the nucleotides in position 1 to position 9 of the miRNA and the corresponding nucleotide sequence in the RNA molecule; three mismatches between any one of the nucleotides in position 12 to position 21 of the miRNA and the corresponding nucleotide sequence in the RNA molecule provided that there are no more than two consecutive mismatches. The chimeric gene may comprise the nucleotide sequence of SEQ ID No 37 from the nucleotide at position 689 to the nucleotide at position 709. The chimeric gene may also comprise the nucleotide sequence of SEQ ID No.: 38, SEQ ID No 40, SEQ ID No.: 41 or SEQ ID No.: 42. The chimeric gene according to the invention may encode a primary transcript capable of being processed into a pre-miRNA whereby the pre-miRNA is derived from a naturally occurring pre-miRNA, such as pre-miR398 and whereby the primary transcript can adopt a secondary RNA structure comprising single-stranded RNA structures and double stranded RNA stems and a pre-miRNA processing signal, such that the junctions between the single stranded RNA structures and the double-stranded RNA stems in the region of the pre-miRNA processing signal are similar to the junctions between the single stranded RNA structures and the double-stranded RNA stems in the region of the pre-miRNA processing signal in the naturally occurring pre-miRNA or pri-mRNA.

The chimeric gene may thus comprise the nucleotide sequence of a naturally occurring pre-miRNA, such as pre-miR398, as a scaffold, i.e. without the naturally occurring miRNA and miRNA* sequence, e.g. the nucleotide sequence of SEQ ID No 41 from nucleotide 1 to nucleotide 33 and the nucleotide sequence of SEQ ID No 41 from nucleotide 55 to nucleotide 97 and the nucleotide sequence of SEQ ID No 41 from nucleotide 119 to nucleotide 147.

In yet another embodiment of the invention, a chimeric gene is provided comprising the following operably linked DNA regions: a plant expressible promoter; a DNA region which upon introduction and transcription in a plant cell is processed into a miRNA, the miRNA being capable of recognizing and guiding the cleavage of the mRNA of an endogenous PARP gene or ParG gene of the plant; and optionally, a 3' DNA region involved in transcription termination and polyadenylation, as well as plant cells and plants comprising such chimeric genes.

The invention also provides a synthetic miRNA capable of recognizing and guiding the cleavage of the mRNA of an endogenous PARP gene or ParG gene of the plant, preferably a miRNA comprising a nucleotide sequence which is essentially complementary to a nucleotide sequence of at least 21 consecutive nucleotides of the endogenous PARP gene or ParG gene of the plant, provided that one or more of following mismatches are allowed: a mismatch between the nucleotide at the 5' end of the miRNA and the corresponding nucleotide sequence in the RNA molecule; a mismatch between any one of the nucleotides in position 1 to position 9 of the miRNA and the corresponding nucleotide sequence in the RNA molecule; three mismatches between any one of the nucleotides in position 12 to position 21 of the miRNA and the corresponding nucleotide sequence in the RNA molecule provided that there are no more than two consecutive mismatches In another embodiment of the invention, a method for reducing the effect of a miRNA on the reduction of the expression of a target gene in a plant cell is provided, comprising the step of providing the plant cell with an excess of a the RNA substrate which is recognized and cleaved by a miRNA, the RNA substrate being recognized and cleaved by the miRNA With the foregoing and other objects, advantages and features of the invention that will become hereinafter apparent, the nature of the invention may be more clearly understood by reference to the following detailed description of different embodiments of the invention, the appended claims and the figures.

BRIEF DESCRIPTION OF THE DRAWINGS

FIG. 2: Comparison of the degree of sequence identity between miRPARP, miRPARP2m and miRPARP3m and the corresponding sequence in the target gene (Parp1 or Parp 2). Panel A: nucleotide sequence of miPARP. Panel B: nucleotide sequence of miPARP2m. Panel C: nucleotide sequence of miPARP3m. MiRPARP2m has two mismatches whereas miRPARPm3 has three mismatches.

FIG. 3: Design of a miRNA capable of recognizing Arabidopsis PARP1 (SEQ ID NO: 53) and PARP2 (SEQ ID NO: 54) genes. Mismatches between the miRNA and the target nucleotide sequences are indicated in a lighter color. Panel miRPARP7 (SEQ ID NO: 55) Bottom miRPARP7 (SEQ ID NO: 38)

FIG. 4: Modification of the premiRNA398a (left) (SEQ ID NO: 39) to incorporate the nucleotide sequence of miR-PARP7 (right) (SEQ ID NO: 40). The microRNA is indicated in bold, the complementary strand of the microRNA is italicized.

FIG. 5: Design of a miRNA capable of recognizing specifically Arabidopsis PARP2 genes (SEQ ID NOs: 56 and 57). Mismatches between the miRNA and the target nucleotide sequences are indicated in a lighter color. Panel miRPARP8 (SEQ ID NO: 58) Bottom miRPARP8 (SEQ ID NO: 41)

FIG. 6: Modification of the premiRNA398a (left) (SEQ ID NO: 39) to incorporate the nucleotide sequence of miR-PARP2-8 (right) (SEQ ID NO: 42). The microRNA is indicated in bold, the complementary strand of the microRNA is italicized.

DETAILED DESCRIPTION OF DIFFERENT EMBODIMENTS

Figure 1:
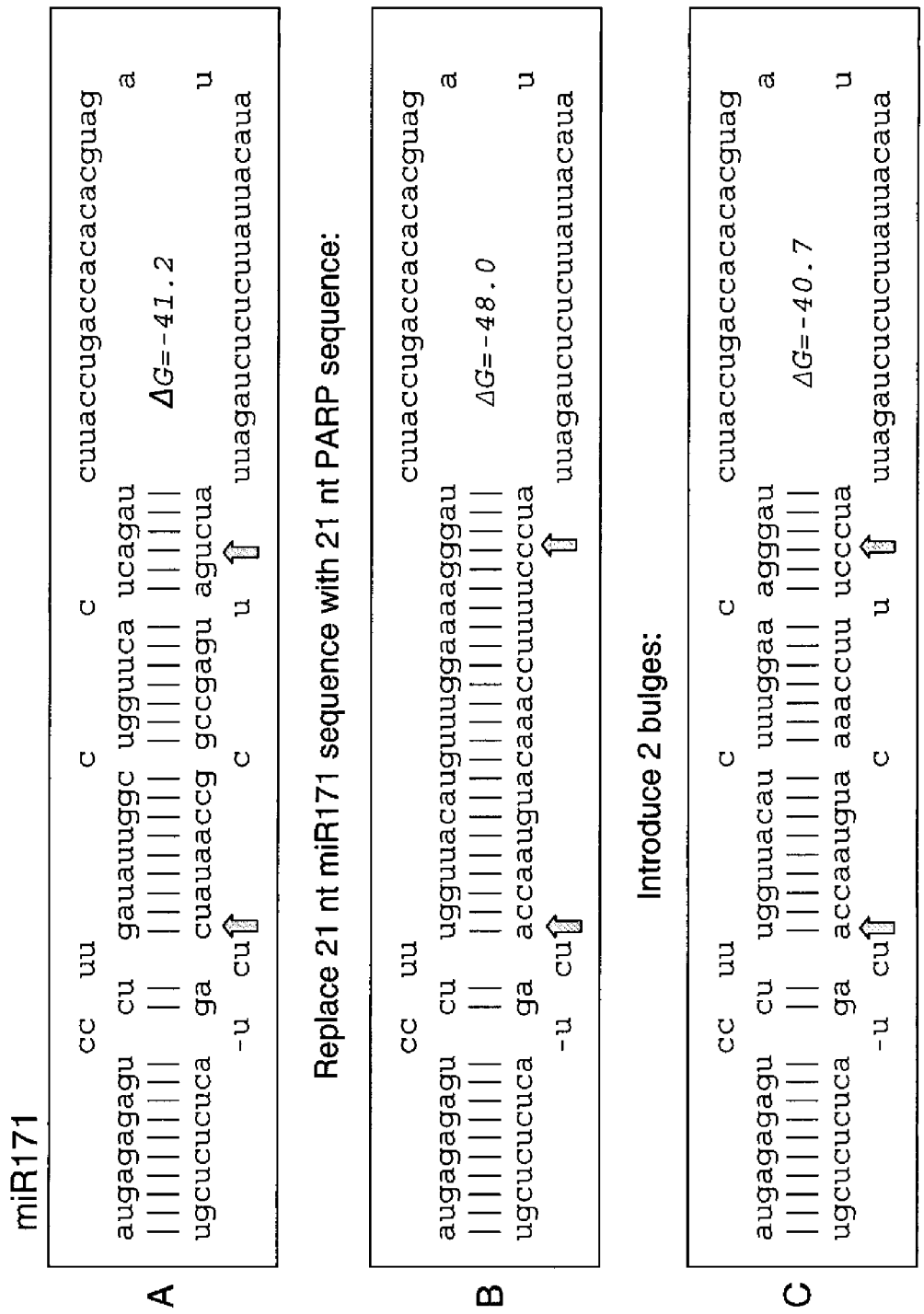
FIG. 1: Schematic representation of the changes to the miRNA 171 scaffold to produce a miRNA targeting endogenous PARP genes. Panel A: nucleotide sequence of the mRNA 171 (SEQ ID NOs: 43 and 44). Panel B: miRNA 171 after replacement of the 21 nt miR171 sequence with the 21 nt PARP sequence (SEQ ID NOs: 45 and 46). Panel C: mRPARP sequence obtained by the introduction of two bulges into the miRNA* sequence (SEQ ID NOs: 47 and 48). ΔG is the free Gibb's energy of the optimal folded RNA structure. The arrows indicate the endpoints of the miRNA sequences.

The current invention is based on the identification of novel miRNA molecules which can reduce the expression of endogenous plant genes which have been demonstrated to be differentially regulated in plants or plant cells subjected to different abiotic stress responses or which have been demonstrated to be differentially regulated in plants or plant cells which have been engineered to be more stress tolerant according to the methods described in WO00/004173 or WO2004/090140. Another aspect of the invention is based on the demonstration that the introduction of a chimeric gene encoding a synthetic miRNA molecule, designed to recognize an endogenous PARP gene as target sequence in a plant is surprisingly efficient enough to achieve downregulation of endogenous PARP genes as described in WO00/004173.

Thus, in a first embodiment, the invention provides miRNA molecules involved in regulating the expression of plant genes which are involved in the response of plant cells to stress conditions, particularly abiotic stress conditions as well as the use of such miRNA molecules to obtain stress tolerant plant cells and plants. Such miRNA include synthetic miRNA molecules directed to cleave the mRNA molecules transcribed from endogenous PARP or PARG encoding genes of the plant cells.

As used herein, a "miRNA" is an RNA molecule of about 20 to 22 nucleotides in length which can be loaded into a RISC complex and direct the cleavage of another RNA molecule, wherein the other RNA molecule comprises a nucleotide sequence essentially complementary to the nucleotide sequence of the miRNA molecule whereby one or more of the following mismatches may occur:

A mismatch between the nucleotide at the 5' end of said miRNA and the corresponding nucleotide sequence in the target RNA molecule;

A mismatch between any one of the nucleotides in position 1 to position 9 of said miRNA and the corresponding nucleotide sequence in the target RNA molecule;

Three mismatches between any one of the nucleotides in position 12 to position 21 of said miRNA and the corresponding nucleotide sequence in the target RNA molecule provided that there are no more than two consecutive mismatches.

No mismatch is allowed at positions 10 and 11 of the miRNA (all miRNA positions are indicated starting from the 5' end of the miRNA molecule).

A miRNA is processed from a "pre-miRNA" molecule by proteins, such as DCL proteins, present in any plant cell and loaded onto a RISC complex where it can guide the cleavage of the target RNA molecules.

Pre-microRNA molecules are usually processed from pri-microRNA molecules (primary transcripts). In animals, microRNA maturation is initiated by the Drosha-DGCR8 complex by precise cleavage of the stem loops that are embedded in primary transcripts. The single stranded RNA segments flanking the pre-microRNA are important for processing of the pri-miRNA into the premiRNA. The cleavage site appears to be determined by the distance from the stem-ssRNA junction (Han et al. 2006, Cell 125, 887-901, 887-901).

As used herein, a "pre-miRNA" molecule is an RNA molecule of about 100 to about 200 nucleotides, preferably about 100 to about 130 nucleotides which can adopt a secondary structure comprising a double stranded RNA stem and a single stranded RNA loop and further comprising the nucleotide sequence of the miRNA (and its complement sequence) in the double stranded RNA stem. Preferably, the miRNA and its complement are located about 10 to about 20 nucleotides from the free ends of the miRNA double stranded RNA stem. The length and sequence of the single stranded loop region are not critical and may vary considerably, e.g. between 30 and 50 nt in length. An example of a synthetic pre-miRNA is represented in FIG. 1. Other examples are represented in FIGS. 4 and 6. Preferably, the difference in free energy between unpaired and paired RNA structure is between −20 and −60 kcal/mole, particularly around −40 kcal/mole. The complementarity between the miRNA and the miRNA* need not be perfect and about 1 to 3 bulges of unpaired nucleotides can be tolerated. The secondary structure adopted by an RNA molecule can be predicted by computer algorithms conventional in the art such as mFOLD. The particular strand of the double stranded RNA stem from the pre-miRNA which is released by DCL activity and loaded onto the RISC complex is determined by the degree of complementarity at the 5' end, whereby the strand which at its 5' end is the least involved in hydrogen bounding between the nucleotides of the different strands of the cleaved dsRNA stem is loaded onto the RISC complex and will determine the sequence specificity of the target RNA molecule degradation. However, if empirically the miRNA molecule from a particular synthetic pre-miRNA molecule is not functional (because the "wrong" strand is loaded on the RISC complex), it will be immediately evident that this problem can be solved by exchanging the position of the miRNA molecule and its complement on the respective strands of the dsRNA stem of the pre-miRNA molecule. As is known in the art, binding between A and U involving two hydrogen bounds, or G and U involving two hydrogen bounds is less strong that between G and C involving three hydrogen bounds.

Naturally occurring miRNA molecules may be comprised within their naturally occurring pre-miRNA molecules but they can also be introduced into existing pre-miRNA molecule scaffolds by exchanging the nucleotide sequence of the miRNA molecule normally processed from such existing pre-miRNA molecule for the nucleotide sequence of another miRNA of interest. The scaffold of the pre-miRNA can also be completely synthetic. Likewise, synthetic miRNA molecules may be comprised within, and processed from, existing pre-miRNA molecule scaffolds or synthetic pre-miRNA scaffolds. Interestingly, it has been observed that some pre-miRNA scaffolds may be preferred over others for their efficiency to be correctly processed into the designed microRNAs, particularly when expressed as a chimeric gene wherein other DNA regions, such as untranslated leader sequences or transcription termination and polyadenylation regions are incorporated in the primary transcript in addition to the pre-microRNA. In particular, it has been found that the transcription of a primary transcript comprising a pre-microRNA and other more or less complementary regions may interfere with the correct processing of the primary transcript into pre-microRNA and ultimately into the designed micro-RNA. Other pre-microRNA scaffolds, such as e.g. premicroRNA398, may be less prone to such incorrect processing. Without intending to limit the invention to a particular mode of action, it is expected that the presence of one or more unstructured single stranded regions at a particular fixed location from the cleavage site of pre-miRNA molecule in an overall mostly double-stranded RNA region, influences the correct processing of the designed pre-miRNA molecules and contributes to the fact that e.g. processing of pre-miR398 derived scaffolds from the primary transcript is less prone to errors than e.g. processing of pre-miR171 derived scaffolds from primary transcripts.

It will be immediately clear to the skilled artisan that the presence of additional sequences may have an influence on the folding of the primary transcript RNA molecule into a secondary RNA structure and particularly on presence and location of bulges or single stranded RNA structures in otherwise doublestranded RNA stem (sub)structures. The location of single-stranded RNA or bulge structures relative to the pre-miRNA, i.e. the distance in nucleotides should be carefully maintained. Secondary RNA structures for a particular RNA nucleotide sequence can easily be predicted using software tools and algorithms well known in the art such as MFOLD (Zucker et al. 2003 Nucleic Acids Research 31, 3406-3415). Furthermore, it is well within the skill of the art to design or modify a nucleotide by substituting nucleotides in a nucleotide sequence such that the newly introduced nucleotides exhibit more or less complementarity to another part of the nucleotide sequence and in this way influence the generation of double-stranded RNA stems or of single stranded RNA bulges.

In one embodiment of the invention, novel miRNA molecules are provided involved in the regulation of plant genes differentially regulated between stressed plants and unstressed plants whereby the miRNA molecules comprise the nucleotide sequence of any one of SEQ ID No. 1 to SEQ ID No. 36. Also provided are variants thereof which are able of guiding the cleavage of at least the same target RNA sequences as the mentioned miRNA molecules according to the above mentioned mismatch rules, as well as pre-miRNA molecules comprising the nucleotide sequence of the miRNA molecules and their variants. The pre-miRNA molecules (and consequently also the miRNA molecules) can be conveniently introduced into a plant cell by providing the plant cells with a gene comprising a plant-expressible promoter operably linked to a DNA region, which when transcribed yields the pre-miRNA molecule. The plant expressible promoter may be the promoter naturally associated with the pre-miRNA molecule or it may be a heterologous promoter.

The novel miRNA molecules, or pre-miRNA processed into such miRNA molecules may be used to modify the regulation of the target genes, and consequently the response of plant cells to adverse growing conditions. In one way, the miRNA molecules occurring in said plant cells may be rendered less or non-functional, leading to an increased expression of the target gene, normally regulated by the novel miRNA. Rendering miRNA molecules less functional or non-functional may be achieved in several ways including selection for variation in the nucleotide sequence of the miRNA encoding sequence (including selection after T-DNA insertion mutagenesis or after induced mutagenesis). Another way of rendering miRNA molecules less functional is to increase the amount of the target RNA molecules (or at least the part thereof recognized by the miRNA). Such an increase in target RNA may be conveniently achieved by providing the plant cells with a chimeric gene comprising a plant-expressible promoter and a DNA region encoding such a target RNA or a part thereof. In another embodiment, a DNA encoding a miRNA resistant target RNA may also be linked to the promoter naturally associated with the pre-miRNA recognizing the target gene and introduced into the plant cell. In this way, the miRNA resistant target RNA will be expressed under the same circumstances as the miRNA and the resistant target RNA will substitute for the non-resistant target RNA degraded by the miRNA induced cleavage. The miRNA resistant target RNA is essentially similar to the target RNA modified to render it resistant to miRNA induced cleavage, e.g. by modifying the sequence thereof such that a variation is introduced in the nucleotide of the target sequence complementary to the nucleotides 10 or 11 of the miRNA resulting in a mismatch. Clearly if the target RNA is an RNA coding for a protein any modification would need to be silent with regard to the coding region or at least result in a substitution yielding a functional protein. Non-functional miRNA alleles or miRNA resistant target genes may also be introduced by homologous recombination to substitute the miRNA encoding alleles or miRNA sensitive target genes.

Silencing of the target genes, or increased reduction of the expression of the target genes can also be achieved by increasing the level of miRNA in the plant cells. Conveniently this can be achieved by providing the plant cells with a chimeric gene comprising the following operably linked DNA fragments:

A plant expressible promoter;
A DNA region which upon introduction and transcription in a plant cell is processed into a novel miRNA according to the invention or a variant thereof; and
optionally, a 3' DNA region involved in transcription termination and polyadenylation In another embodiment of the invention a method is provided for increasing the resistance of plants to adverse growing conditions whereby the cells of the plants are provided with a synthetic miRNA molecule which is capable of recognizing and guiding the cleavage of the mRNA transcribed from an endogenous PARP gene or PARG gene of the plant. Preferably, such a miRNA molecule comprises a nucleotide sequence nucleotide sequence which is essentially complementary to a nucleotide sequence of at least 21 consecutive nucleotides of a PARP or PARG gene, preferably the endogenous PARP gene or ParG gene of the plant (including any of the plant PARP or PARG sequences hereinafter described), provided that one or more of following mismatches are allowed:

A mismatch between the nucleotide at the 5' end of said miRNA and the corresponding nucleotide sequence in the RNA molecule;
A mismatch between any one of the nucleotides in position 1 to position 9 of said miRNA and the corresponding nucleotide sequence in the RNA molecule;
Three mismatches between any one of the nucleotides in position 12 to position 21 of said miRNA and the corresponding nucleotide sequence in the RNA molecule provided that there are no more than two consecutive mismatches.
No mismatch is allowed at positions 10 and 11 of the miRNA Such a miRNA can conveniently be provided to the plant in the form of a pre-miRNA comprising the nucleotide sequence of the miRNA in its double stranded RNA stem, as described elsewhere in this application. The pre-miRNA scaffold can be from an existing pre-miRNA or be a synthetic, man-made pre-miRNA scaffold. Most conveniently, a DNA region encoding such a pre-miRNA comprising the miRNA is operably linked to a plant-expressible promoter and optionally a 3' end involved in transcription termination and polyadenylation and introduced in a plant cell in a manner well known in the art (including transformation or crossing).

As used herein "a stress tolerant plant" or "a plant tolerant to stress conditions or adverse growing conditions" is a plant (particularly a plant obtained according to the methods of the invention), which, when subjected to adverse growing conditions for a period of time, such as but not limited to drought, high temperatures, limited supply of nutrients (particularly nitrogen), high light intensities, grows better than a control plant not treated according to the methods of the invention. This will usually be apparent from the general appearance of the plants and may be measured e.g., by increased biomass production, continued vegetative growth under adverse conditions or higher seed yield. Stress tolerant plant have a broader growth spectrum, i.e. they are able to withstand a broader range of climatological and other abiotic changes, without yield penalty. Biochemically, stress tolerance may be apparent as the higher $NAD^+$-NADH/ATP content and lower production of reactive oxygen species of stress tolerant plants compared to control plants under stress condition. Stress tolerance may also be apparent as the higher chlorophyll content, higher photosynthesis and lower chlorophyll fluorescence under stress conditions in stress tolerant plants compared to control plants under the same conditions.

It will be clear that it is also not required that the plant be grown continuously under the adverse conditions for the stress tolerance to become apparent. Usually, the difference in stress tolerance between a plant or plant cell according to the invention and a control plant or plant cell will become apparent even when only a relatively short period of adverse conditions is encountered during growth.

The following database entries identifying experimentally demonstrated and putative poly ADP-ribose polymerase protein sequences, parts thereof or homologous sequences, could be identified: BAD53855 (*Oryza sativa*); BAD52929 (*Oryza sativa*); XP_477671 (*Oryza sativa*); BAC84104 (*Oryza sativa*); MT25850 (*Zea mays*); AAT25849 (*Zea mays*); NP_197639 (*Arabidopsis thaliana*); NP_850165 (*Arabidopsis thaliana*); NP_188107 (*Arabidopsis thaliana*); NP_850586 (*Arabidopsis thaliana*); BAB09119 (*Arabidopsis thaliana*); AAD20677 (*Arabidopsis thaliana*); Q11207 (*Arabidopsis thaliana*); C84719 (*Arabidopsis thaliana*); T51353 (*Arabidopsis thaliana*); T01311 (*Arabidopsis thaliana*); AAN12901 (*Arabidopsis thaliana*); AAM13882 (*Arabidopsis thaliana*); CAB80732 (*Arabidopsis thaliana*); CAA10482 (*Arabidopsis thaliana*); AAC79704 (*Zea mays*): AAC19283 (*Arabidopsis thaliana*); CAA10888 (*Zea mays*); CAA10889 (*Zea mays*); CAA88288 (*Arabidopsis thaliana*).

For the purpose of the invention, PARP proteins are defined as proteins having poly (ADP-ribose) polymerase activity, preferably comprising the so-called "PARP signature". The PARP signature is an amino acid sequence which is highly conserved between PARP proteins, defined by de Murcia and Menussier de Murcia (1994) as extending from amino acid at position 858 to the amino acid at position 906 from the *Mus musculus* PARP protein. This domain corresponds to the amino acid sequence from position 817 to 865 of the conventional PARP protein of *Zea mays* (ZAP1; SEQ ID No 2 of WO 00/04173 herein incorporated by reference) or to the amino acid sequence from position 827 to 875 of the conventional PARP protein of *Zea mays* (ZAP2; SEQ ID No 11 of WO 00/04173 herein incorporated by reference) or to the amino acid sequence from position 500 to 547 of the non-conventional PARP protein of *Zea mays* (SEQ ID No 4 of WO 00/04173 herein incorporated by reference) or to the amino acid sequence from position 485 to 532 of the non-conventional PARP protein of *Arabidopsis thaliana* (SEQ ID No 6 of WO 00/04173 herein incorporated by reference). This amino sequence is highly conserved between the different PARP proteins (having about 90% to 100% sequence identity). Particularly conserved is the lysine at position 891 (corresponding to position 850 of SEQ ID No 2 of WO 00/04173 herein incorporated by reference, position 861 of SEQ ID No 11 of WO 00/04173 herein incorporated by reference, position 532 of SEQ ID No 4 of WO 00/04173 herein incorporated by reference, position 517 of SEQ ID No 6 of WO 00/04173 herein incorporated by reference) of the PARP protein from *Mus musculus*, which is considered to be involved in the catalytic activity of PARP proteins. Particularly the amino acids at position 865, 866, 893, 898 and 899 of the PARP protein of *Mus musculus* or the corresponding positions for the other sequences are variable. PARP proteins may further comprise an N-terminal DNA binding domain and/or a nuclear localization signal (NLS).

Currently, two classes of PARP proteins have been described. The first class, as defined herein, comprises the so-called classical Zn-finger containing PARP proteins (ZAP). These proteins range in size from 113-120 kDA and are further characterized by the presence of at least one, preferably two Zn-finger domains located in the N-terminal domain of the protein, particularly located within the about 355 to about 375 first amino acids of the protein. The Zn-fingers are defined as peptide sequences having the sequence CxxCxnHxxC (whereby n may vary from 26 to 30) capable of complexing a Zn atom. Examples of amino acid sequences for PARP proteins from the ZAP class include the sequences which can be found in the PIR protein database with accession number P18493 (*Bos taurus*), P26466 (*Gallus gallus*), P35875 (*Drosophila melanogaster*), P09874 (*Homo sapiens*), P11103 (*Mus musculus*), Q08824 (*Oncorynchus masou*), P27008 (*Rattus norvegicus*), Q11208 (*Sarcophaga peregrina*), P31669 (*Xenopus laevis*) and the currently identified sequences of the ZAP1 and ZAP2 protein from *Zea mays* (SEQ ID No 2 of WO 00/04173 herein incorporated by reference/SEQ ID No 11 of WO 00/04173 herein incorporated by reference).

The nucleotide sequence of the corresponding cDNAs can be found in the EMBL database under accession numbers D90073 (*Bos taurus*), X52690 (*Gallus gallus*), D13806 (*Drosophila melanogaster*), M32721 (*Homo sapiens*), X14206 (*Mus musculus*), D13809 (*Oncorynchus masou*), X65496 (*Rattus norvegicus*), D16482 (*Sarcophaga peregrina*), D14667 (*Xenopus laevis*) and in SEQ ID No 1 and 10 (*Zea mays*).

The second class as defined herein, comprises the so-called non-classical PARP proteins (NAP). These proteins are smaller (72-73 kDa) and are further characterized by the absence of a Zn-finger domain at the N-terminus of the protein, and by the presence of an N-terminal domain comprising stretches of amino acids having similarity with DNA binding proteins. Preferably, PARP protein of these class comprise at least one amino acid sequence of about 30 to 32 amino acids which comprise the sequence R G x x x x G x K x x x x x R L (SEQ ID NO: 59) (amino acids are represented in the standard one-letter code, whereby x stands for any amino acid; SEQ ID No 7 of WO 00/04173 herein incorporated by reference). Even more preferably these PARP proteins comprise at least 1 amino acid sequence of about 32 amino acids having the sequence x L x V x x x R x x L x x R G L x x x G V K x x L V x R L x x x A I (SEQ ID NO: 60) (SEQ ID No 8 of WO 00/04173 herein incorporated by reference) (the so-called A1 domain) or at least 1 amino acid sequence of about 32 amino acids having the sequence G M x x x E L x x x A x x R G x x x x G x K K D x x R L x x (SEQ ID NO: 61) (SEQ ID No 9 of WO 00/04173 herein incorporated by reference) (the so-called A2 domain) or both. Particularly, the A1 and A2 domain are capable of forming a helix-loop-helix structure. These PARP proteins may further comprise a basic "B" domain (K/R rich amino acid sequence of about 35 to about 56 amino acids, involved in targeting the protein to the nucleus) and/or a an acid "C" domain (D/E rich amino acid sequence of about 36 amino acids). Examples of protein sequences from the NAP class include the APP protein from *Arabidopsis thaliana* (accessible from PIR protein database under accession number Q11207; SEQ ID No 6 of WO 00/04173 herein incorporated by reference) and the NAP protein from *Zea mays* (SEQ ID No 4). The sequence of the corresponding cDNAs can be found in the EMBL database under accession number Z48243 (SEQ ID No 5 of WO 00/04173 herein incorporated by reference) and in SEQ ID No 3 of WO 00/04173 herein incorporated by reference.

It is clear that for the purpose of the invention, other genes or cDNAs encoding PARP proteins from both classes as defined, or parts thereof, can be isolated or identified from other plant species or varieties, particularly from other plant species or varieties. These PARP genes or cDNAs can be isolated e.g. by Southern hybridization (either low-stringency or high-stringency hybridization depending on the relation between the species from which one intends to isolate the PARP gene and the species from which the probe was ultimately derived) using as probes DNA fragments with the nucleotide sequence of the above mentioned PARP genes or cDNAs, or parts thereof, preferably parts which are conserved such as a gene fragment comprising the nucleotide sequence encoding the PARP signature mentioned supra. The nucleotide sequences corresponding to the PARP signature from the PARP proteins encoded by plant genes are the nucleotide sequence of SEQ ID No 1 of WO 00/04173 herein incorporated by reference from nucleotide 2558 to 2704 or the nucleotide sequence of SEQ ID No 3 of WO 00/04173 herein incorporated by reference from nucleotide 1595 to 1747 or the nucleotide sequence of SEQ ID No 5 of WO 00/04173 herein incorporated by reference from nucleotide 1575 to 1724. If a discrimination is to be made between the classes of PARP genes, parts of the PARP genes which are specific for the class, such as the N-terminal domains preceding the catalytic domain or parts thereof, should preferably be used.

Alternatively, the genes or cDNAs encoding PARP proteins or parts thereof, can also be isolated by PCR-amplification using appropriate primers such as the degenerated primers with the nucleotide sequence corresponding to the sequences indicated in SEQ ID No 13 of WO 00/04173 herein incorporated by reference, SEQ ID No 14 of WO 00/04173 herein incorporated by reference, or primers with the nucleotide sequence corresponding to the sequences indicated in SEQ ID No 15 to 20 of WO 00/04173 herein incorporated by reference. However, it is clear that the person skilled in the art can design alternative oligonucleotides for use in PCR or can use oligonucleotides comprising a nucleotide sequence of at least 20, preferably at least about 30, particularly at least about 50, consecutive nucleotides of any of the PARP genes to isolate the genes or part thereof by PCR amplification.

It is clear that a combination of these techniques, or other techniques (including e.g. RACE-PCR), available to the skilled artisan to isolate genes or cDNAs on the basis of partial fragments and their nucleotide sequence, e.g. obtained by PCR amplification, can be used to isolate PARP genes, or parts thereof, suitable for use in the methods of the invention.

Moreover, PARP genes, encoding PARP proteins wherein some of the amino acids have been exchanged for other, chemically similar, amino acids (so-called conservative substitutions), or synthetic PARP genes (which encode similar proteins as natural PARP genes but with a different nucleotide sequence, based on the degeneracy of the genetic code) and parts thereof are also suited for the methods of the invention.

The nucleotide sequence of the parp2 gene or parp2 cDNA may comprises the nucleotide sequence of any one the parp2 variants identified in cotton varieties including the nucleotide sequence of SEQ ID No.: 5 of WO2006/045633, herein incorporated by reference, SEQ ID No.: 6 of WO2006/045633, herein incorporated by reference, SEQ ID No.: 7 of WO2006/045633, herein incorporated by reference, SEQ ID No.: 8 of WO2006/045633, herein incorporated by reference, SEQ ID No.: 9 of WO2006/045633, herein incorporated by reference, SEQ ID No.: 10 of WO2006/045633, herein incorporated by reference, SEQ ID No.: 11 of WO2006/045633, herein incorporated by reference, SEQ ID No.: 12 of WO2006/045633, herein incorporated by reference, SEQ ID No.: 18 of WO2006/045633, herein incorporated by reference, SEQ ID No.:19 of WO2006/045633, herein incorporated by reference or SEQ ID No.:20 of WO2006/045633, herein incorporated by reference or a nucleotide sequence encoding a protein comprising the amino acid sequence of SEQ ID No.: 13 of WO2006/045633, herein incorporated by reference, SEQ ID No.: 21 of WO2006/045633, herein incorporated by reference or SEQ ID No.:22 of WO2006/045633, herein incorporated by reference or a variant thereof As used herein, a "PARG encoding gene" or a "ParG gene" is a gene capable of encoding a PARG (poly ADP ribose glycohydrolase) protein, wherein the PARG protein catalyzes the depolymerization of poly ADP-ribose, by releasing free ADP ribose units either by endoglycolytic or exoglycolytic action.

PARG encoding genes may comprise a nucleotide sequence encoding a protein comprising the amino acid sequence of SEQ ID No 1 of WO2004/090140, herein incorporated by reference (*Arabidopsis thaliana*) or of SEQ ID No 2 (*Solanum tuberosum*) or of SEQ ID No 16 of WO2004/090140, herein incorporated by reference (*Oryza sativa*) or parts thereof, such as a DNA fragment comprising the nucleotide sequence of SEQ ID No. 3 of WO2004/090140, herein incorporated by reference or SEQ ID 4 of WO2004/090140, herein incorporated by reference or SEQ ID No 15. or SEQ ID 23 of WO2004/090140, herein incorporated by reference (*Zea mays*).

However, it will be clear that the skilled person can isolate variant DNA sequences from other plant species, by hybridization with a probe derived from the above mentioned PARG encoding genes from plant species, or even with a probe derived from the above mentioned PARG encoding genes from animal species. To this end, the probes should preferably have a nucleotide sequence comprising at least 40 consecutive nucleotides from the coding region of those mentioned PARG encoding genes sequences, preferably from the coding region of SEQ ID No 3 of WO2004/090140, herein incorporated by reference or SEQ ID No 4 of WO2004/090140, herein incorporated by reference. The probes may however comprise longer regions of nucleotide sequences derived from the ParG genes, such as about 50, 60, 75, 100, 200 or 500 consecutive nucleotides from any of the mentioned ParG genes. Preferably, the probe should comprise a nucleotide sequence coding for one of the highly conserved regions of the catalytic domain, which have been identified by aligning the different PARG proteins from animals. These regions are also present in the identified PARG protein from *Arabidopsis thaliana* and comprise the amino acid sequence LXVDFANXXXGGG (SEQ ID NO: 62) (corresponding to SEQ ID No 1 of WO2004/090140, herein incorporated by reference from the amino acid at position 252 to the amino acid at position 264; X may be any amino acid) LXVDFANXXXGGGXXXXGXVQEEIRF (SEQ ID NO: 63) (corresponding to SEQ ID No 1 of WO2004/090140, herein incorporated by reference from the amino acid at position 252 to the amino acid at position 277) or LXVDFANXXXGGGXXXXGXVQEEIRFXXXPE (SEQ ID NO: 64) (corresponding to SEQ ID No 1 of WO2004/090140, herein incorporated by reference from the amino acid at position 252 to the amino acid at position 282), TGXWGCGXFXGD (SEQ ID NO: 65) (corresponding to SEQ ID No 1 from the amino acid at position 449 to the amino acid at position 460) or TGXWGCGAFXGDXXLKXXXQ (SEQ ID NO: 66) (corresponding to SEQ ID No 1 of WO2004/090140, herein incorporated by reference from the amino acid at position 449 to the amino acid at position 468). Other conserved regions have the amino acid sequence DXXXRXXXXAIDA (SEQ ID NO: 67) (corresponding to SEQ ID No 1 of WO2004/090140, herein incorporated by reference from the amino acid at position 335 to the amino acid at position 344) or REXXKAXXGF (SEQ ID NO: 68)

(corresponding to SEQ ID No 1 of WO2004/090140, herein incorporated by reference from the amino acid at position 360 to the amino acid at position 369) or GXXXXSXYTGY (SEQ ID NO: 69) (corresponding to SEQ ID No 1 of WO2004/090140, herein incorporated by reference from the amino acid at position 303 to the amino acid at position 313). Hybridization should preferably be under stringent conditions.

"Stringent hybridization conditions" as used herein mean that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared carrier DNA such as salmon sperm DNA, followed by washing the hybridization support in 0.1×SSC at approximately 65° C., e.g. for about 10 min (twice). Other hybridization and wash conditions are well known and are exemplified in Sambrook et al, Molecular Cloning: A Laboratory Manual, Second Edition, Cold Spring Harbor, N.Y. (1989), particularly chapter 11.

Alternatively, ParG encoding genes or parts thereof may also be isolated by PCR based techniques, using as primers oligonucleotides comprising at least 20 consecutive nucleotides from a nucleotide sequence of the mentioned PARG encoding genes or the complement thereof. Such primers may comprise a nucleotide sequence encoding a conserved region, as mentioned above, or be complementary to such a nucleotide sequence. Oligonucleotides which may be used for that purpose may comprise the nucleotide sequence of either or SEQ ID No. 5 of WO2004/090140, herein incorporated by reference, SEQ ID No 6 of WO2004/090140, herein incorporated by reference., SEQ ID No. 7 of WO2004/090140, herein incorporated by reference or SEQ ID No. 8 of WO2004/090140, herein incorporated by reference. Oligonucleotides which may be used may also be degenerate, such as the oligonucleotide primers of SEQ ID No 17, SEQ ID No 18, SEQ ID No 19; SEQ ID No 20, SEQ ID No 21 or SEQ ID No 22, all of WO2004/090140, herein incorporated by reference.

Specific PCR fragments from ParG genes may e.g., be obtained by using combinations of the oligonucleotides having the nucleotide sequence of SEQ ID No. 5 of WO2004/090140, herein incorporated by reference and SEQ ID No 6 of WO2004/090140, herein incorporated by reference using e.g., *Arabidopsis* genomic DNA or cDNA as a template DNA, or by using combinations of the oligonucleotides having the nucleotide sequence of SEQ ID No. 7 of WO2004/090140, herein incorporated by reference and SEQ ID No 8 of WO2004/090140, herein incorporated by reference using e.g., potato genomic DNA or cDNA as a template DNA, under stringent annealing conditions.

The isolated sequences may encode a functional PARG protein or a part thereof. Preferably the isolated sequences should comprise a nucleotide sequence coding for one or more of the highly conserved regions from the catalytic domain of PARG proteins as mentioned elsewhere.

However, for the purpose of the invention is not required that the isolated sequences encode a functional ParG protein nor that a complete coding region is isolated. Indeed, all that is required for the invention is that a chimeric gene can be designed or produced, based on the identified or isolated sequence of the endogenous ParG gene from a plant, which is capable of producing a ParG inhibitory RNA. Several alternative methods are available to produce such a ParG inhibitory RNA molecule.

It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

As used herein, "the nucleotide sequence of a PARP encoding gene or of a PARG encoding gene" usually refers to the nucleotide sequence of the DNA strand corresponding in sequence to the nucleotide sequence of the mRNA molecule transcribed from such a PARP or PARG gene, unless specified otherwise.

PARG encoding genes have been identified in a number of animals such as *Rattus norvegicus* (Accession numbers: NM_031339, NW_043030, AB019366), *Mus musculus* (Accession numbers: NT_039598, NM_003631, AF079557), *Homo sapiens* (Accession numbers: NT_017696; NM_003631, AF005043), *Bos taurus* (Accession numbers: NM_174138, U78975) *Drosophila melanogaster* (Accession number: AF079556)

In plants, a poly(ADP-ribose) glycohydrolase has been identified by map-based cloning of the wild-type gene inactivated in a mutant affected in clock-controlled transcription of genes in *Arabidopsis* and in photoperiod dependent transition from vegetative growth to flowering (tej). The nucleotide sequence of the gene can be obtained from nucleotide databases under the accession number AF394690 (Panda et al., 2002 Dev. Cell. 3, 51-61).

As used herein, the term "promoter" denotes any DNA which is recognized and bound (directly or indirectly) by a DNA-dependent RNA-polymerase during initiation of transcription. A promoter includes the transcription initiation site, and binding sites for transcription initiation factors and RNA polymerase, and can comprise various other sites (e.g., enhancers), at which gene expression regulatory proteins may bind.

The term "regulatory region", as used herein, means any DNA, that is involved in driving transcription and controlling (i.e., regulating) the timing and level of transcription of a given DNA sequence, such as a DNA coding for a protein or polypeptide. For example, a 5' regulatory region (or "promoter region") is a DNA sequence located upstream (i.e., 5') of a coding sequence and which comprises the promoter and the 5'-untranslated leader sequence. A 3' regulatory region is a DNA sequence located downstream (i.e., 3') of the coding sequence and which comprises suitable transcription termination (and/or regulation) signals, including one or more polyadenylation signals.

In one embodiment of the invention the promoter is a constitutive promoter. In another embodiment of the invention, the promoter activity is enhanced by external or internal stimuli (inducible promoter), such as but not limited to hormones, chemical compounds, mechanical impulses, abiotic or biotic stress conditions. The activity of the promoter may also regulated in a temporal or spatial manner (tissue-specific promoters; developmentally regulated promoters).

For the purpose of the invention, the promoter is a plant-expressible promoter. As used herein, the term "plant-expressible promoter" means a DNA sequence which is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S (Hapster et al., 1988), the subterranean clover virus promoter No 4 or No 7 (WO9606932), or T-DNA gene promoters but also tissue-specific or organ-specific promoters including but not limited to seed-specific promoters (e.g., WO89/03887), organ-primordia specific promoters (An et al., 1996), stem-specific promoters (Keller et al., 1988), leaf specific promoters (Hudspeth et al., 1989), mesophyl-specific promoters (such as the light-inducible Rubisco promoters), root-specific promoters (Keller et al., 1989), tuber-specific promoters (Keil et al., 1989), vascular tissue specific promoters (Peleman et al., 1989), stamen-selective promoters (WO 89/10396, WO 92/13956), dehiscence zone specific promoters (WO 97/13865) and the like.

Methods for the introduction of chimeric genes into plants are well known in the art and include *Agrobacterium*-mediated transformation, particle gun delivery, microinjection, electroporation of intact cells, polyethyleneglycol-mediated protoplast transformation, electroporation of protoplasts, liposome-mediated transformation, silicon-whiskers mediated transformation etc. The transformed cells obtained in this way may then be regenerated into mature fertile plants.

The plant cells and plant lines according to the invention may further comprise chimeric genes which will reduce the expression of PARP genes as described in WO 00/04173 or chimeric genes which will reduce the expression of PARG genes as described in WO 2004/090140. These further chimeric genes may be introduced e.g. by crossing the transgenic plant lines of the current invention with transgenic plants containing PARP gene expression reducing chimeric genes. Transgenic plant cells or plant lines may also be obtained by introducing or transforming the chimeric genes of the invention into transgenic plant cells comprising the PARP gene expression reducing chimeric genes or vice versa. Alternatively, the PARP and PARG inhibitory RNA regions may be encoded by one chimeric gene and transcribed as one RNA molecule.

The chimeric genes encoding the pre-miRNA molecules as described herein may be subject to posttranscriptional or transcriptional silencing as any introduced chimeric gene. However, methods are available in the art to identify silencing, including determining the presence of 21-24 nt single stranded RNA molecules preferably hybridized by probes recognizing both the microRNA and the microRNA*. Such silenced transgenic lines should preferably be avoided.

The chimeric genes of the invention (or the miRNA molecules corresponding thereto) may also be introduced into plant cells in a transient manner, e.g using the viral vectors, such as viral RNA vectors as described in WO 00/63397 or WO 02/13964.

It is also an object of the invention to provide plant cells and plants containing the chimeric genes or the RNA molecules according to the invention. Gametes, seeds, embryos, either zygotic or somatic, progeny or hybrids of plants comprising the chimeric genes of the present invention, which are produced by traditional breeding methods are also included within the scope of the present invention.

The plants obtained by the methods described herein may be further crossed by traditional breeding techniques with other plants to obtain stress tolerant progeny plants comprising the chimeric genes of the present invention.

The methods and means described herein are believed to be suitable for all plant cells and plants, both dicotyledonous and monocotyledonous plant cells and plants including but not limited to cotton, Brassica vegetables, oilseed rape, wheat, corn or maize, barley, alfalfa, peanuts, sunflowers, rice, oats, sugarcane, soybean, turf grasses, barley, rye, sorghum, sugar cane, vegetables (including chicory, lettuce, tomato, zucchini, bell pepper, eggplant, cucumber, melon, onion, leek), tobacco, potato, sugarbeet, papaya, pineapple, mango, *Arabidopsis thaliana*, but also plants used in horticulture, floriculture or forestry (poplar, fir, eucalyptus etc.).

To the extent necessary, all nucleotide sequences or amino acid sequences referred herein by their accession number in the publicly available databases are herein incorporated by reference.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region which is functionally or structurally defined, may comprise additional DNA regions etc.

The following non-limiting Examples describe method and means for increasing stress tolerance in plants according to the invention.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Throughout the description and Examples, reference is made to the following sequences:
SEQ ID No.:1 cDNA of miRNA mb01-a01
SEQ ID No.:2 cDNA of miRNA mb01-b04
SEQ ID No.:3: cDNA of miRNA mb01-b09
SEQ ID No.:4 cDNA of miRNA mb01-h09
SEQ ID No.:5 cDNA of miRNA mb02-c04
SEQ ID No.:6 cDNA of miRNA mb02-g01
SEQ ID No.:7 cDNA of miRNA mb03-h06
SEQ ID No.:8 cDNA of miRNA mb04-d07
SEQ ID No.:9 cDNA of miRNA mb04-g09
SEQ ID No.:10 cDNA of miRNA mb06-c04
SEQ ID No.:11 cDNA of miRNA mb06-f06
SEQ ID No.:12 cDNA of miRNA mb06-h03
SEQ ID No.:13 cDNA of miRNA mb07-b12
SEQ ID No.:14 cDNA of miRNA mb07-c01
SEQ ID No.:15 cDNA of miRNA mb07-e03
SEQ ID No.:16 cDNA of miRNA mb08-e11
SEQ ID No.:17 cDNA of miRNA mb08-g02
SEQ ID No.:18 cDNA of miRNA mb08-h02
SEQ ID No.:19 cDNA of miRNA mb09-h05
SEQ ID No.:20 cDNA of miRNA mb10-b02
SEQ ID No.:21 cDNA of miRNA mb10-d05
SEQ ID No.:22 cDNA of miRNA mb10-g05
SEQ ID No.:23 cDNA of miRNA mb11-c05

SEQ ID No.:24 cDNA of miRNA mb11-d04
SEQ ID No.:25 cDNA of miRNA mb11-e04
SEQ ID No.:26 cDNA of miRNA mb13-c11
SEQ ID No.:27 CDNA of miRNA mb14-a09
SEQ ID No.:28 CDNA of miRNA mb15-a06
SEQ ID No.:29 CDNA of miRNA mb16-g11
SEQ ID No.:30 CDNA of miRNA mb17-e10
SEQ ID No.:31 CDNA of miRNA mb18-b02
SEQ ID No.:32 CDNA of miRNA mb18-e02
SEQ ID No.:33 CDNA of miRNA mb18-h12
SEQ ID No.:34 CDNA of miRNA mb19-d08
SEQ ID No.:35 cDNA of miRNA mb19-g05
SEQ ID No.:36 CDNA of miRNA mb20-c07
SEQ ID No.:37 nucleotide sequence of a chimeric gene encoding miRPARP and variations thereof in miRPARPm2 and miRPARPm3
SEQ ID No.:38: nucleotide sequence of miRPARP7
SEQ ID No.:39: nucleotide sequence of pre-microRNA 398a
SEQ ID No.: 40: nucleotide sequence of pre-microRNA 398a engineered to be processed into miRPARP7.
SEQ ID No.:41: nucleotide sequence of miRPARP7
SEQ ID No.: 42: nucleotide sequence of pre-microRNA398a engineered to be processed into miRPARP2-8.

EXAMPLES

Example 1

Identification of Novel miRNA Molecules Involved in Abiotic Stress Responses in Plants Two cDNA libraries were constructed, according to methods standard in the art, from either unstressed *A. thaliana* 2 week old seedlings or from 2 week old *A. thaliana* seedlings which had been subjected to high light conditions. Only the RNA fraction comprising molecules of about 15 to 30 nucleotides in length were used.

Random cDNA clones were sequenced. These sequences were first filtered to retain only those which contained cDNA corresponding to RNA of about 20 to 25 nucleotides in length. The remaining sequences were compared to the *A. thaliana* genomic sequence (using BLAST) to discard sequences having sequence identity to ribosomal RNA sequences, tRNA sequences, chloroplast or mitochondrial RNA sequences. This analysis also revealed for the remaining sequences, the corresponding loci in the *Arabidopsis* genome from which the potential miRNA molecules could originate.

Using FastA algorithm against the database of *Arabidopsis* coding regions, possible target sequences having sequence similarity (but allowing for mismatches) could be identified.

In a next step the genomic regions corresponding to the genomic location of the retained small RNA molecules were analyzed for secondary structure using mFold to identify pre-miRNA-like structures.

Of the remaining potential miRNA structures, the expression pattern of the corresponding target sequences under stressed and non-stressed conditions were analyzed, and those miRNA structures which had a target gene differentially expressed in stressed versus non-stressed plants were retained. These miRNAs and corresponding target genes are indicated in Table 1.

Chimeric gene are constructed encoding pre-miRNA structures comprising the miRNA sequences of Table 1, expressed under control of a strong constitutive promoter. Transgenic plants comprising these chimeric genes are constructed and the effect on stress tolerance of the transgenic plants is analyzed.

TABLE 1

| miRNA | sequence | length | target sequence |
|---|---|---|---|
| mb01-a01 | ACAGTGACCCGGCCCGAACTCT (SEQ ID No.: 1) | 22 | At1g67070 phosphomannose isomerase - putative (DIN9) |
| mb01-b04 | GCAACGGTTTATTATCCATCCC (SEQ ID No.: 2) | 22 | At3g60660 expressed protein At3g47350 short-chain dehydrogenase - reductase (SDR) At5g04940 SET domain-containing protein (SUVH1) At1g73100 SET domain-containing protein (SUVH3) At4g02630 protein kinase family protein |
| mb01-b09 | CTAAACGTTCCAAGTGCATCC (SEQ ID No.: 3) | 21 | AtMg00890 hypothetical protein At5g16070 chaperonin - putative At1g19250 flavin-containing monooxygenase At5g65630 DNA-binding bromodomain-containing protein |
| mb01-h09 | TTTGAAAGGAGAGGAATGGAAG (SEQ ID No.: 4) | 22 | At4g18270 glycosyl transferase family 4 |
| mb02-c04 | TTGCTGTTGGTACCGCTGATC (SEQ ID No.: 5) | 21 | At5g62090 expressed protein |

TABLE 1-continued

| miRNA | sequence | length | target sequence |
|---|---|---|---|
| mb02-g01 | TGGTGATGAAGTTGATTGGTT (SEQ ID No.: 6) | 21 | At5g04360 pullulanase - putative At5g03150 zinc finger (C2H2 type) |
| mb03-h06 | GGTTTTGGGTGCGATTTTGGTT (SEQ ID No.: 7) | 22 | At5g22500 acyl CoA reductase - putative At1g64160 disease resistance-responsive |
| mb04-d07 | GATCTCTTCTTCTTTCTCTGC (SEQ ID No.: 8) | 21 | At5g46795 expressed protein At5g27640 eukaryotic translation initiation factor 3 subunit 9 At5g17910 expressed protein At3g55060 expressed protein At3g09980 expressed protein At5g40700 expressed protein predicted At3g10400 RNA recognition motif (RRM)-containing protein |
| Mb04-g09 | GCTCCCTTTGGGGTAAAGCCCT (SEQ ID No.: 9) | 22 | At3g06895 expressed protein |
| Mb06-c04 | ATAAACCTCCCCGATTTTTG (SEQ ID No.: 10) | 20 | At1g17100 SOUL heme-binding family protein At2g11000 natC N(alpha)-terminal acetyltransferase At1g59960 aldo - keto reductase |
| Mb06-f06 | GCTGCAGCAAGCCCGAGTAGTT (SEQ ID No.: 11) | 22 | At5g08660 expressed protein At3g60190 dynamin-like protein E (DL1E) At5g22280 expressed protein |
| Mb06-h03 | ATCCGTAATGGTGTGGATCC (SEQ ID No.: 12) | 20 | At2g46860 inorganic pyrophosphatase At5g04970 pectinesterase At1g10970 metal transporter - putative (ZIP4) |
| Mb07-b12 | GGAGGGTCCTGCTTTCGAGTGG (SEQ ID No.: 13) | 22 | At2g24280 serine carboxypeptidase S28 |
| Mb07-c01 | CGGGTTTGGCAGAACGTTACTT (SEQ ID No.: 14) | 22 | At4g31910 transferase family protein At3g45990 actin-depolymerizing factor |
| Mb07-e03 | AAAAATCGGCGGGGGAGAGTG (SEQ ID No.: 15) | 21 | At2g06000 pentatricopeptide (PPR) repeat-containing protein At3g18380 expressed protein |
| Mb08-e11 | AGATAGCTGAAGGTGACTCGGG (SEQ ID No.: 16) | 22 | At3g10650 expressed protein |
| Mb08-g02 | AAAATCCAAAAACTGAATCG (SEQ ID No.: 17) | 20 | At1g36150 protease inhibitor - seed storage - lipid transfer protein (LTP) At5g24400 glucosamine - galactosamine-6-phosphate isomerase At3g58580 endonuclease - exonuclease - phosphatase family |

TABLE 1-continued

| miRNA | sequence | length | target sequence |
|---|---|---|---|
| | | | At3g10575 pseudogene - similar to putative 3-phosphoinositide-dependent protein kinase-1 At2g46550 expressed protein At4g02410 lectin protein kinase family protein At1g31480 shoot gravitropism 2 (SGR2) |
| Mb08-h02 | AATCATCTCCAAGGAGACATC (SEQ ID No.: 18) | 21 | Atg32290 beta-amylase - putative At2g30280 expressed protein At1g66140 zinc finger (C2H2 type) |
| Mb09-h05 | GCTTTAAATCGGGATGAAAC (SEQ ID No.: 19) | 20 | At4g36450 mitogen-activated protein kinase - putative - MAPK At1g04450 p21-rho-binding domain-containing protein At4g08800 protein kinase - putative similar to dual specificity kinase 1 At3g53930 protein kinase family protein At2g06040 expressed protein |
| Mb10-b02 | AAATCTCGATCATCAAACCGT (SEQ ID No.: 20) | 21 | At1g19090 serine - threonine protein kinase (RKF2) At1g15380 lactoylglutathione lyase family protein At3g47990 zinc finger (C3HC4-type RING finger) |
| Mb10-d05 | GGGCTCCGATGAAATTGAATTG (SEQ ID No.: 21) | 22 | At1g48650 helicase domain-containing protein |
| Mb10-g05 | TCGGTGGATCTTAGAAAATT (SEQ ID No.: 22) | 20 | At5g61930 expressed protein contains Pfam PF05634 |
| Mb11-c05 | TTTAGCCACTTACGAGGATCTC (SEQ ID No.: 23) | 22 | At4g03580 hypothetical protein At1g60700 forkhead-associated domain-containing protein |
| Mb11-d04 | GATGAGGAAGAGGATGAGGAAG (SEQ ID No.: 24) | 22 | At5g01310 basic helix-loop-helix (bHLH) family protein At4g18760 leucine-rich repeat family protein At1g77720 protein kinase family protein At3g57880 C2 domain-containing protein At3g18770 expressed protein |
| Mb11-e04 | CATCCGGTCAGCATCATCAGT (SEQ ID No.: 25) | 21 | At1g28180 pseudogene - putative RNA helicase At3g51830 phosphoinositide phosphatase family protein At4g19185 integral membrane family protein |

TABLE 1-continued

| miRNA | sequence | length | target sequence |
|---|---|---|---|
| Mb13-c11 | TTGTGATTGTGGGGAAGGATG (SEQ ID No.: 26) | 21 | At5g03555<br>permease - cytosine - purines - uracil - thiamine - allantoin<br>At2g46560<br>transducin family protein - WD-40 repeat<br>At4g12000<br>expressed protein |
| Mb14-a09 | AGACGGTTTTCTAAAAGCTTG (SEQ ID No.: 27) | 21 | At1g68190<br>zinc finger (B-box type)<br>At3g59060<br>basic helix-loop-helix (bHLH) family protein<br>At1g23340<br>expressed protein similar to At1g70550 |
| Mb15-a06 | CTGGTTTAGTCACTTTCACTG (SEQ ID No.: 28) | 21 | At3g26100<br>regulator of chromosome condensation (RCC1) |
| Mb16-g11 | CGATTCCCCGCACCTCCACC (SEQ ID No.: 29) | 20 | At4g12070<br>expressed protein<br>At2g34990<br>zinc finger (C3HC4-type RING finger)<br>At5g65820<br>pentatricopeptide (PPR) repeat-containing protein<br>At1g29790<br>expressed protein |
| Mb17-e10 | CCAGTTCGCCCGTAGTGTGCCC (SEQ ID No.: 30) | 22 | At5g29070<br>expressed protein<br>At4g07932<br>hypothetical protein<br>At3g21120<br>F-box family protein |
| Mb18-b02 | GAGAAATGGAAGATATCGTG (SEQ ID No.: 31) | 20 | At5g38275<br>pseudogene - similar to SCUTL1<br>At5g09560<br>KH domain-containing protein<br>At5g16250<br>expressed protein |
| Mb18-e02 | TACCTGGTTCGATCCTGCCAGT (SEQ ID No.: 32) | 21 | At3g48720<br>transferase family protein similar to hypersensitivity-related hsr201<br>At4g32430<br>pentatricopeptide (PPR) repeat-containing protein<br>At1g58050<br>helicase domain-containing protein |
| Mb18-h12 | GTTTCAAGCGTCACTCGAACCG (SEQ ID No.: 33) | 22 | At3g47770<br>ABC transporter family protein |
| Mb19-d08 | GTGGAGATCGTGGAGAAGCGG (SEQ ID No.: 34) | 21 | At3g48460<br>GDSL-motif lipase - hydrolase family protein<br>At1g75680<br>glycosyl hydrolase family 9 protein<br>At2g17010<br>mechanosensitive ion channel domain-containing protein<br>At5g54630<br>zinc finger protein-related |
| Mb19-g05 | AAGGGAAAGCGAGAAAAGGGAG (SEQ ID No.: 35) | 22 | At1g07410<br>Ras-related GTP-binding protein |
| Mb20-c07 | TTGAATTGAAGTGCTTGAATT (SEQ ID No.: 36) | 21 | At1g61230<br>pseudogene - jacalin lectin family<br>At1g52130<br>jacalin lectin family protein<br>At1g57570 |

TABLE 1-continued

| miRNA sequence | length | target sequence |
|---|---|---|
| | | jacalin lectin family protein At1g33790 |
| | | jacalin lectin family protein At5g49850 |
| | | jacalin lectin family protein At1g52060 |
| | | jacalin lectin family protein At5g28520 |
| | | jacalin lectin family protein At1g52050 |
| | | jacalin lectin family protein At1g52070 |
| | | jacalin lectin family protein At1g60110 |
| | | jacalin lectin family protein At1g52110 |
| | | pseudogene - jacalin lectin family At5g49870 |
| | | jacalin lectin family protein At2g25980 |
| | | jacalin lectin family protein At1g16880 |
| | | uridylyltransferase-related |

Example 2

Construction of a Chimeric Gene Encoding a Synthetic miRNA Molecule Targeting Endogenous PARP Genes A synthetic pre-miRNA nucleotide sequence was designed based on the pre-miRN171 scaffold and comprising a miRNA sequence complementary to a 21 nucleotide sequence conserved (identical) between the parp1 and parp2 coding region of *A. thaliana*. This nucleotide sequence is located in so-called PARP signature domain. To this end, the miRNA nucleotide sequence of pre-miR171 scaffold (FIG. 1; panel A) was replaced with the nucleotide sequence complementary to the PARP1/PARP2 conserved sequence (FIG. 1; panel B) and corresponding nucleotide changes were made in the miRNA* containing strand. Finally, two nucleotide changes were introduced in the miRNA* strand resulting in mismatches in the dsRNA stem, introducing two bulges at locations where bulges occur in the natural pre-miRNA171 (FIG. 1; panel C). The resulting corresponding DNA nucleotide sequence was synthesized using standard techniques.

Using standard recombinant techniques a chimeric gene was constructed having the following operably linked DNA fragments:

A CaMV35S promoter (SEQ ID No.: 37 from nt 1 to 531)
An untranslated leader sequence (Cab22L; SEQ ID No.: 37 from nt 531 to 591)
A DNA region comprising the modified pre-mi171 comprising the miRPARP (SEQ ID No.: 37 from nt 592 to 737)
The 3' end region of the CaMV 35S transcript. (SEQ ID No.:37 from nt 737 to 958

Similar chimeric genes were constructed wherein the nucleotide sequence of the miRPARP was modified to introduce mismatches between the miRNA molecule and the target PARP1/PARP2 nucleotide sequence (see FIG. 2, panels B and C). The following nucleotides were substituted:

In miRPARP2m:
nt 619: G->A
nt 630: G->A
nt 695: C->T
nt 706: C->T
In miRPARP3m
nt 619: G->A
nt 620: T->G
nt 630: G->A
nt 695: C->T
nt 705: A->C
nt 706: C->T

The chimeric genes were introduced into *A. thaliana* plants and transgenic lines comprising the different chimeric genes were generated. Seedlings from the different transgenic lines as well as from untransformed control plants and positive control stress-tolerant lines, were allowed to grow under optimal conditions for two weeks, and than subjected to high light stress for 3 days. The weight of 25 seedlings per line was determined and is represented in table 2.

TABLE 2 miRPARP high light stress experiment:

| Plant Line | Weight |
|---|---|
| Col-0 (control) | 400 |
| miRPARPm3 line 1 | 460 |
| miRPARPm2 line 1 | 593 |
| miRPARP line 1 | 595 |
| miRPARPm3 line 1 | 627 |
| Positive control 1 (transgenic line as described in WO 00/04173) | 641 |
| miRPARP line 2 | 757 |
| miRPARP line 3 | 759 |
| Positive control 2 (transgenic line as described in WO 00/04173) | 769 |
| miRPARP line 4 | 798 |

All miRNA comprising transgenic lines exhibited a significantly higher weight than the untransformed control line after growing 3 days under high light stress conditions. The increase in stress tolerance was similar to that obtained by downregulating PARP genes using dsRNA encoding chimeric genes described in WO 00/04173.

Total nucleic acids were isolated using CTAB in a conventional manner and separated on a 15% acrylamide/urea gel and probed with LNA oligonucleotide probes recognizing either the microRNA strand or the complementary microRNA* strand. No 21 nt oligonucleotides could be detected, but a 80 nt long processed RNA sequence hybridizing to a probe recognizing miRPARP2 was identified in different transgenic lines. Most likely these results indicate a problem with the correct processing of the pre-microRNA.

Figure 3:
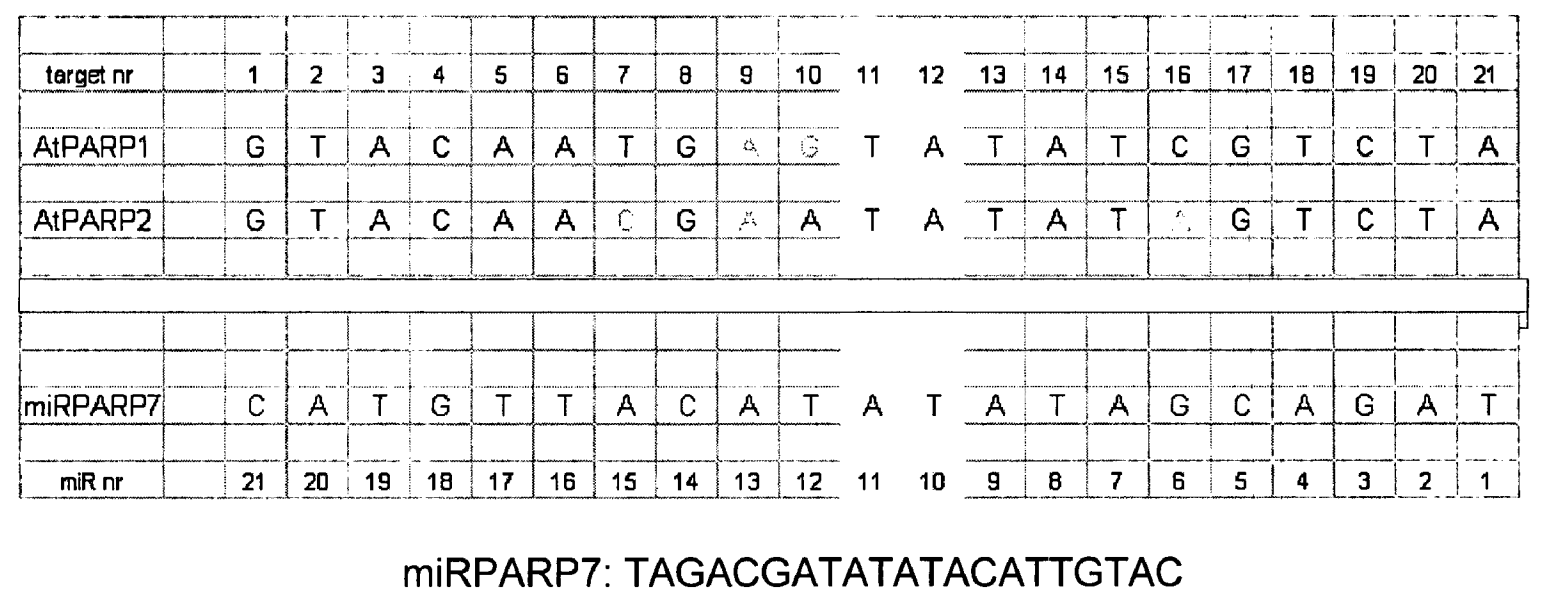

Another synthetic pre-miRNA nucleotide sequence was designed based on the pre-miRNA398a scaffold and comprising a miRNA sequence complementary to a 21 nucleotide sequence conserved (identical) between the parp1 and parp2 coding region of A. thaliana. To this end, the miRNA nucleotide sequence of pre-miR398a scaffold (FIG. 4; left panel) was replaced with the nucleotide sequence complementary to the PARP1/PARP2 conserved sequence (FIG. 3) and corresponding nucleotide changes were made in the miRNA* containing strand. The resulting corresponding DNA nucleotide sequence (SEQ ID No 40) was synthesized using standard techniques.

Using standard recombinant techniques a chimeric gene was constructed having the following operably linked DNA fragments:
A CaMV35S promoter (SEQ ID No.: 37 from nt 1 to 531)
An untranslated leader sequence (Cab22L; SEQ ID No.: 37 from nt 531 to 591)
A DNA region comprising the modified pre-mi398a comprising the miRPARP7 (SEQ ID No.: 40)
The 3' end region of the CaMV 35S transcript. (SEQ ID No.:37 from nt 737 to 958)

The chimeric gene was introduced into A. thaliana plants and transgenic lines comprising the different chimeric genes were generated.

Total nucleic acid from different transgenic lines were isolated using CTAB in a conventional manner and separated on a 15% acrylamide/urea gel and probed with LNA oligonucleotide probes recognizing either the microRNA strand or the complementary microRNA* strand. Single stranded nucleotides of 21 and 24 nucleotides in length were identified, which hybridized either with the microRNA probe and the microRNA* probe. This indicates that pre-miRPARP7 is not processed as a natural miRNA. Moreover, this may indicate that transcriptional and/or posttranscriptional silencing of the introduced miRNA encoding chimeric gene occurs.

Yet another synthetic pre-miRNA nucleotide sequence was designed based on the pre-miRNA398a scaffold and comprising a miRNA sequence complementary to a 21 nucleotide sequence specific for the parp2 coding region of A. thaliana. To this end, the miRNA nucleotide sequence of pre-miR398a scaffold (FIG. 6; left panel) was replaced with the nucleotide sequence complementary to the PARP2 specific sequence (FIG. 5) and corresponding nucleotide changes were made in the miRNA* containing strand. The resulting corresponding DNA nucleotide sequence (SEQ ID No 42) was synthesized using standard techniques.

Using standard recombinant techniques a chimeric gene was constructed having the following operably linked DNA fragments:
A CaMV35S promoter (SEQ ID No.: 37 from nt 1 to 531)
An untranslated leader sequence (Cab22L; SEQ ID No.: 37 from nt 531 to 591)
A DNA region comprising the modified pre-mi398a comprising the miRPARP2-8 (SEQ ID No.: 42)
The 3' end region of the CaMV 35S transcript. (SEQ ID No.:37 from nt 737 to 958)

The chimeric gene was introduced into A. thaliana plants and transgenic lines comprising the different chimeric genes were generated.

Figure 7:
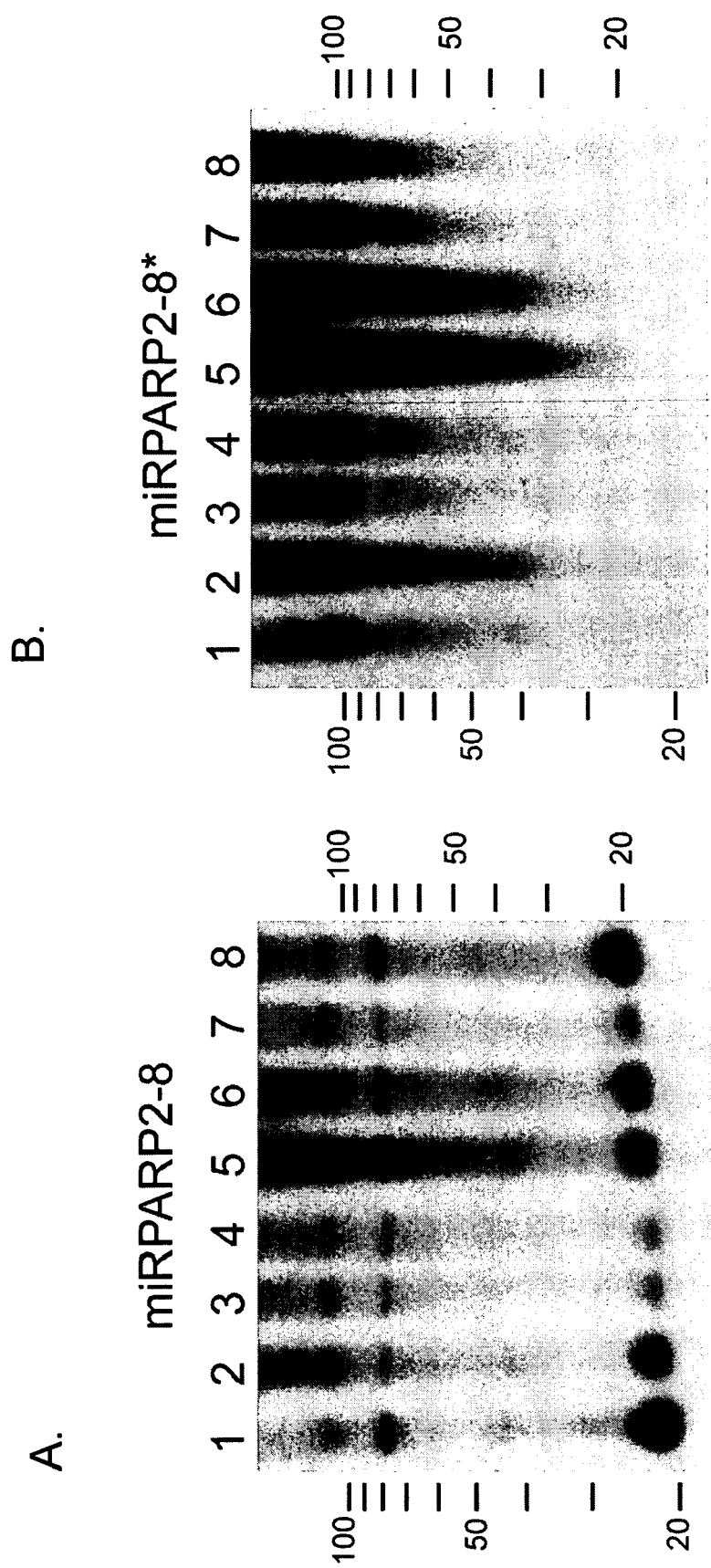
FIG. 7: Northern blot to identify processed microRNA of 21 nucleotides in transgenic Arabidopsis expressing a chimeric gene yielding pre-microRNA2-8. Left panel (A): hybridized with an oligonucleotide probe specifically recognizing the miRPARP2-8; right panel (B) hybridized with an oligonucleotide probe specifically recognizing the miR-PARP2-8* strand.

Total nucleic acid from different transgenic lines were isolated using CTAB in a conventional manner and separated on a 15% acrylamide/urea gel and probed with LNA oligonucleotide probes recognizing either the microRNA strand or the complementary microRNA* strand. The results are represented in FIG. 7. Single stranded nucleotides of 21 nucleotides in length were identified, when hybridized with the microRNA recognizing probe (Panel A) but not when hybridized with the microRNA* recognizing probe. This indicates that pre-miRPARP2-8 is correctly processed similar to a natural miRNA.

Figure 8:
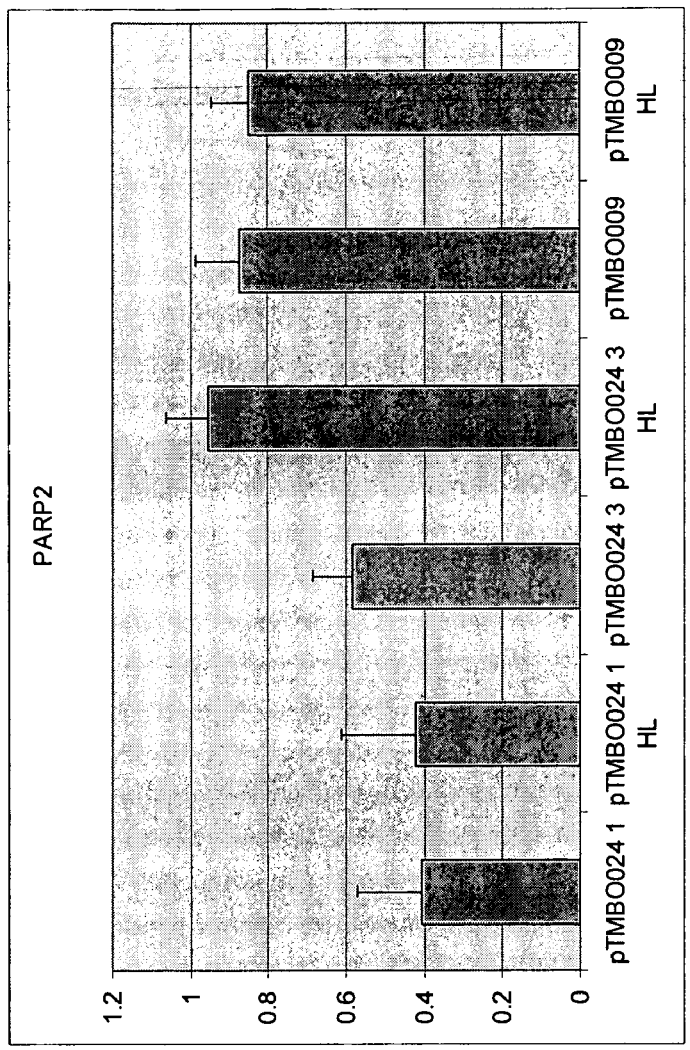
FIG. 8: RT-PCR quantification to detect PARP2 mRNA accumulation in transgenic Arabidopsis expressing the pre-microRNA2-8 chimeric gene. pTMBO024-1 and pTMBO024-3 are different transgenic lines while pTMBO009 is a transgenic line comprising an unrelated transgene. HL refers to growth under high light conditions prior to the isolation of the mRNA.

RT-PCR was performed on mRNA obtained from a control line (pTMBO009) or transgenic lines comprising the miRPARP2-8 encoding chimeric genes (pTMBO024-1 and pTMBO024-3) using primers specific to amplify AtPARP2 nucleotide sequences. The mRNA was obtained from plants which were either grown under normal light conditions, or stressed plants grown under high light conditions (HL). FIG. 8 is a graphic representation of the level of parp2 mRNA detected in the different lines under different conditions. pTMBO024 exhibited a reduced level of parp2 mRNA both under normal and stressed conditions, whereas pTMO024-3 exhibited a reduced level of parp2 mRNA only under normal conditions.

Plants of line pTMO024-1 are subjected to various abiotic stress conditions. The reduced expression of PARP2, or the absence of induction of PARP2 expression under stressed conditions indicates a high stress resistance.

Figure 9:
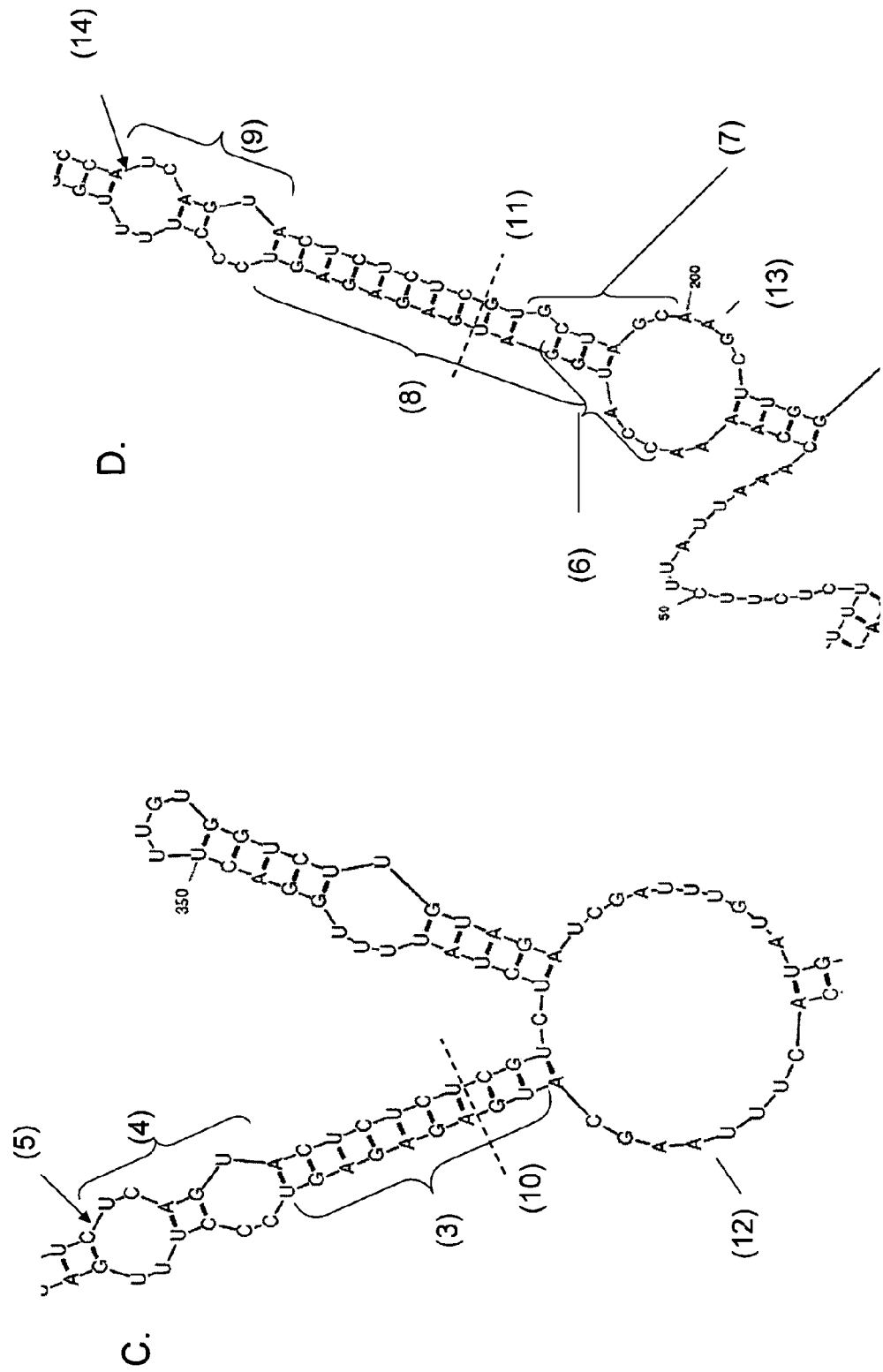
FIG. 9: Panel A: predicted secondary RNA structure of the unmodified primary transcript (pri-miR171) which is processed into pre-miR171 (1) and ultimately into miR171. Panel B: predicted secondary RNA structure of the transcript which is processed into pre-miRPARP (2) and ultimately into miRPARP. Panel C: enlargement of the boxed structure of panel A at the pre-miR171 processing site (10). (3): double stranded RNA stem of about 8 nucleotides in length. (4) and (12) single stranded unpaired RNA structure; (5) endpoint of processed miRNA171. Panel D: enlargement of the boxed structure of panel B at the pre-miRPARP processing site (11). (6): NcoI cloning site; (7) NheI cloning site; (8) double stranded RNA stem of about 12 nucleotides in length; (9) and (13): single stranded unpaired RNA structure; (14): predicted endpoint of processed miRNAPARP.
Figure 10:
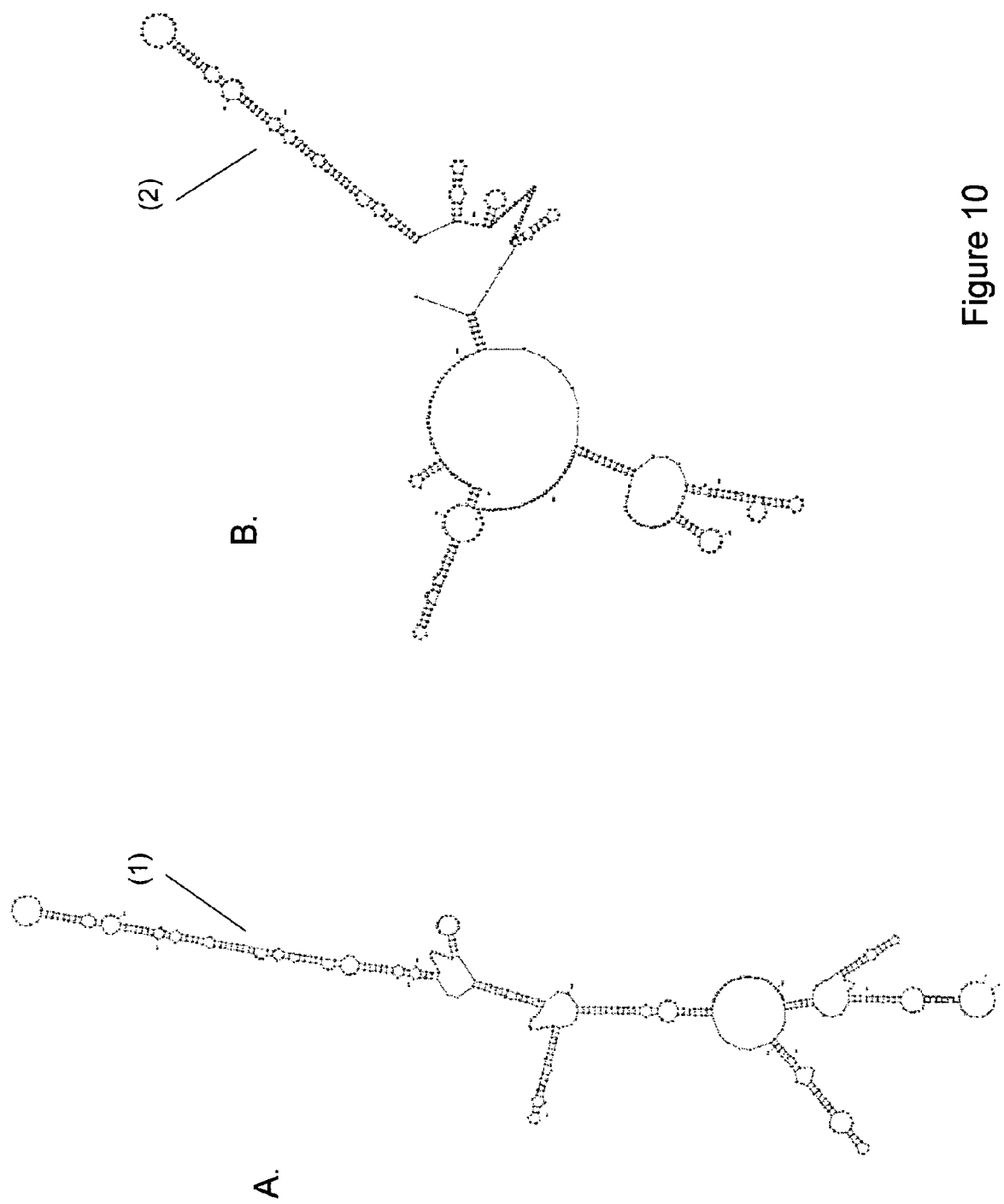
FIG. 10: Panel A: predicted secondary RNA structure of the unmodified primary transcript (pri-miR398) which is processed into pre-miR398 (1) and ultimately into miR398. Panel B: predicted secondary RNA structure of the transcript which is processed into pre-miRPARP2-8 (2) and ultimately into miRPARP2-8. Panel C: enlargement of the boxed structure of panel A at the pre-miR398 processing site (11). (4): double stranded RNA stem of about 7 nucleotides in length. (5) and (13) single stranded unpaired RNA structure; (3) endpoint of processed miRNA398. Panel D: enlargement of the boxed structure of panel B at the pre-miRPARP2-8 processing site (12). (6): single stranded unpaired RNA structure (7); (8) unstructured RNA region of about 7 nucleotides; (9): predicted endpoint of processed miRPARP; (10): NheI and NcoI cloning sites are located behind the single strand RNA bulge.
Figure 10:
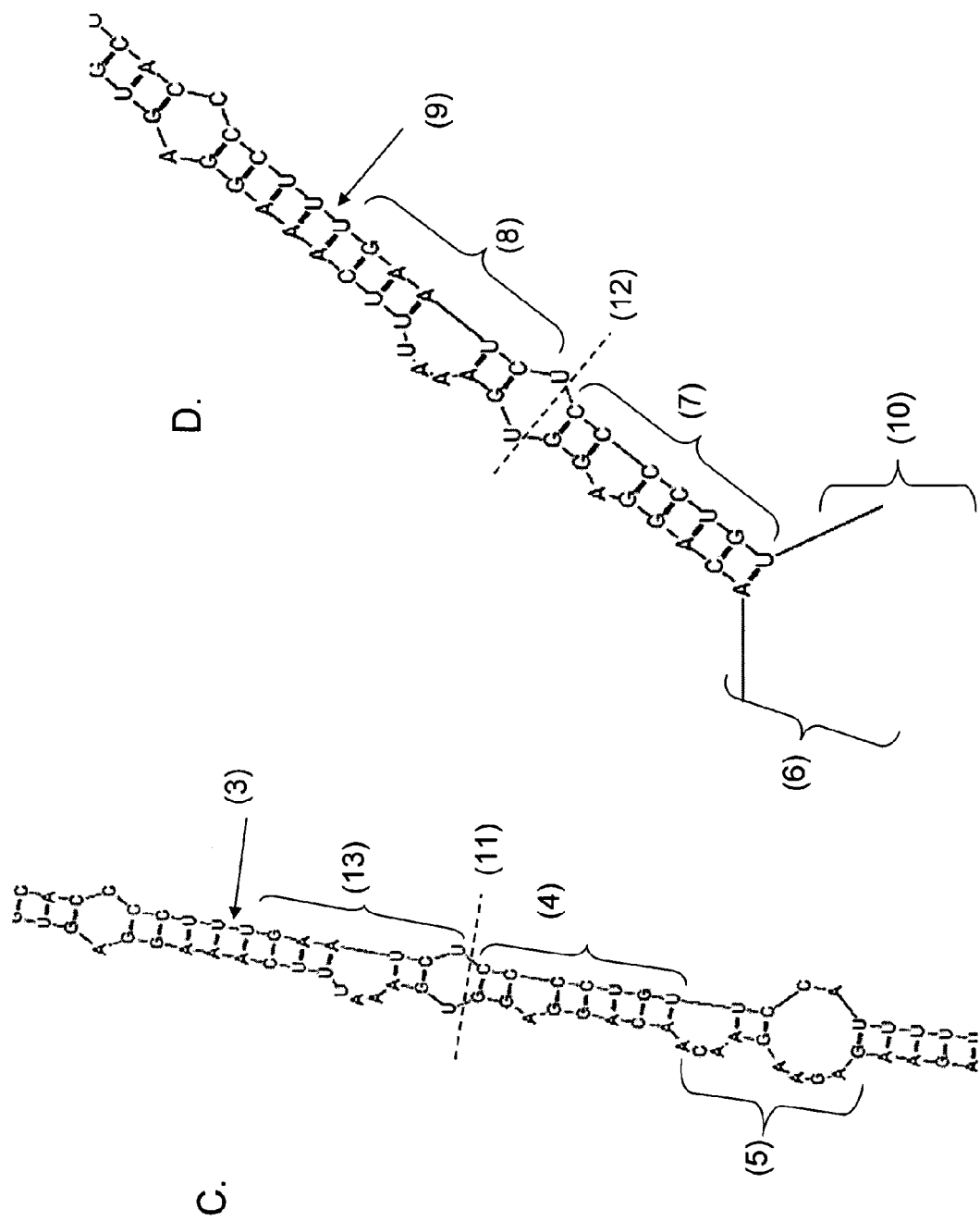

FIG. 9 represents secondary structure for primary transcripts of pri-miR171 (FIG. 9 A), pri-miR171-derived pri-miRPARP7 (FIG. 9B), and respective enlarged portions surrounding the pre-miR171 and pre-miRPARP7 processing site (FIGS. 9 C and D). FIG. 10 represents secondary structure for primary transcripts of pri-miR398 (FIG. 10 A), pri-miR398-derived pri-miRPARP2-8 (FIG. 10 B), and respective enlarged portions surrounding the pre-miR398 and pre-miRPARP2-8 processing site (FIGS. 10 C and D). In both instances, the secondary structure of the primary transcript for the wild type scaffold and the modified scaffold is considerably different; however, the secondary structure of the pre-miRNA substructures (1, 2 in both figures) is relatively well conserved. Nevertheless, close examination of the secondary structure around the pre-miRNA processing site (FIGS. 9 C&D and 10 C&D) reveals that the distance of the junction between single stranded RNA structures (12) and (13) and single stranded RNA structures (4) and (9) and double stranded RNA stems (3, 8) relative to the pre-miRNA processing site (100, 11) has been changed when adapting the pre-miR171 scaffold to incorporate the miRPARP7 sequence. In particular, the double stranded RNA stem (8) in pri-miPARP7 has been increased in length due to the presence of partially complementary nucleotides sequences (6) and (7). This may lead to a processing of pre-miRNA in the synthetic molecule at a different location than in the original pri-mRN171, which in turn may influence the processing of the correct designed miRNA from the synthetic pre-miRNA. On the contrary, the junctions between single stranded structures (5, 13, 6 and 8) and the double stranded RNA stem (4), (7) in the pri-miR398 and derivative pri-miRPARP2-8 are well conserved in relative location. Pri-miRPARP2-8 appears to be correctly processed to pre-miRPARP2-8 and miR-PARP2-8, underlining the importance of maintaining the junctions between the single stranded RNA structures and double-stranded RNA stems in the region of the pre-miRNA processing similar in structure to the pri-miRNA scaffold used.

The invention claimed is:

1. A method of producing a plant tolerant to high light stress, comprising the steps of:
   (a) transforming plant cells with a chimeric gene to create transgenic plant cells, said chimeric gene comprising in sequence the following operably linked DNA fragments:
      (i) a plant-expressible promoter;
      (ii) a DNA region encoding a synthetic miRNA precursor consisting of the nucleotide sequence as set forth in SEQ ID NO: 42; and
      (iii) a 3' end region involved in transcription termination and polyadenylation;
   (b) regenerating a population of transgenic plant lines from said transgenic plant cells, wherein said chimeric gene is transcribed to yield PARP2 inhibitory miRNA from said synthetic miRNA precursor; and
   (c) identifying a plant line within said population of transgenic plant lines, which is tolerant to high light stress conditions as compared to a plant of the same species that does not comprise said chimeric gene.

2. The method according to claim 1, wherein said plant-expressible promoter is a constitutive promoter, a tissue specific promoter, or an inducible promoter.

3. A chimeric gene comprising in sequence the following operably linked DNA fragments:
   (i) a plant-expressible promoter;
   (ii) a DNA region encoding a synthetic miRNA precursor consisting of the nucleotide sequence as set forth in SEQ ID NO: 42; and
   (iii) a 3' end region involved in transcription termination and polyadenylation; and wherein transcription of said chimeric gene yields PARP2 inhibitory miRNA from said synthetic miRNA precursor.

4. A plant cell transformed with the chimeric gene according to claim 3.

5. A plant transformed with the chimeric gene according to claim 3.

6. The chimeric gene according to claim 3, wherein said plant-expressible promoter is a constitutive promoter, a tissue specific promoter, or an inducible promoter.

* * * * *

SEQUENCE LISTING

<160> NUMBER OF SEQ ID NOS: 69

<210> SEQ ID NO 1
<211> LENGTH: 22
<212> TYPE: DNA
<213> ORGANISM: Artificial
<220> FEATURE:
<223> OTHER INFORMATION: microRNA mb01-a01

<400> SEQUENCE: 1
acagtgaccc ggcccgaact ct                                              22

<210> SEQ ID NO 2
<211> LENGTH: 22
<212> TYPE: DNA
<213> ORGANISM: Artificial
<220> FEATURE:
<223> OTHER INFORMATION: microRNA mb01-b04

<400> SEQUENCE: 2
gcaacggttt attatccatc cc                                              22

<210> SEQ ID NO 3
<211> LENGTH: 21
<212> TYPE: DNA
<213> ORGANISM: Artificial
<220> FEATURE:
<223> OTHER INFORMATION: microRNA mb01-b09

<400> SEQUENCE: 3
ctaaacgttc caagtgcatc c                                               21

<210> SEQ ID NO 4
<211> LENGTH: 22
<212> TYPE: DNA
<213> ORGANISM: Artificial
<220> FEATURE:
<223> OTHER INFORMATION: microRNA mb01-h09

<400> SEQUENCE: 4
tttgaaagga gaggaatgga ag                                              22

<210> SEQ ID NO 5
<211> LENGTH: 21
<212> TYPE: DNA
<213> ORGANISM: Artificial
<220> FEATURE:
<223> OTHER INFORMATION: microRNA mb02-c04

<400> SEQUENCE: 5
ttgctgttgg taccgctgat c                                               21

<210> SEQ ID NO 6
<211> LENGTH: 21
<212> TYPE: DNA
<213> ORGANISM: Artificial
<220> FEATURE:
<223> OTHER INFORMATION: microRNA mb02-g01

<400> SEQUENCE: 6
tggtgatgaa gttgattggt t                                               21

<210> SEQ ID NO 7
<211> LENGTH: 22
<212> TYPE: DNA

<213> ORGANISM: Artificial
<220> FEATURE:
<223> OTHER INFORMATION: microRNA mb03-h06

<400> SEQUENCE: 7
ggttttgggt gcgatttgg tt                                               22

<210> SEQ ID NO 8
<211> LENGTH: 21
<212> TYPE: DNA
<213> ORGANISM: Artificial
<220> FEATURE:
<223> OTHER INFORMATION: microRNA mb04-d07

<400> SEQUENCE: 8
gatctcttct tctttctctg c                                               21

<210> SEQ ID NO 9
<211> LENGTH: 22
<212> TYPE: DNA
<213> ORGANISM: Artificial
<220> FEATURE:
<223> OTHER INFORMATION: microRNA mb04-g09

<400> SEQUENCE: 9
gctccctttg gggtaaagcc ct                                              22

<210> SEQ ID NO 10
<211> LENGTH: 20
<212> TYPE: DNA
<213> ORGANISM: Artificial
<220> FEATURE:
<223> OTHER INFORMATION: microRNA mb06-c04

<400> SEQUENCE: 10
ataaacctcc ccgattttg                                                  20

<210> SEQ ID NO 11
<211> LENGTH: 22
<212> TYPE: DNA
<213> ORGANISM: Artificial
<220> FEATURE:
<223> OTHER INFORMATION: microRNA mb06-f06

<400> SEQUENCE: 11
gctgcagcaa gcccgagtag tt                                              22

<210> SEQ ID NO 12
<211> LENGTH: 20
<212> TYPE: DNA
<213> ORGANISM: Artificial
<220> FEATURE:
<223> OTHER INFORMATION: microRNA mb06-h03

<400> SEQUENCE: 12
atccgtaatg gtgtggatcc                                                 20

<210> SEQ ID NO 13
<211> LENGTH: 22
<212> TYPE: DNA
<213> ORGANISM: Artificial
<220> FEATURE:
<223> OTHER INFORMATION: microRNA mb07-b12

<400> SEQUENCE: 13
ggagggtcct gctttcgagt gg                                              22

```
<210> SEQ ID NO 14
<211> LENGTH: 22
<212> TYPE: DNA
<213> ORGANISM: Artificial
<220> FEATURE:
<223> OTHER INFORMATION: microRNA mb07-c01

<400> SEQUENCE: 14
cgggtttggc agaacgttac tt                                           22

<210> SEQ ID NO 15
<211> LENGTH: 21
<212> TYPE: DNA
<213> ORGANISM: Artificial
<220> FEATURE:
<223> OTHER INFORMATION: microRNA mb07-e03

<400> SEQUENCE: 15
aaaaatcggc gggggagagt g                                            21

<210> SEQ ID NO 16
<211> LENGTH: 22
<212> TYPE: DNA
<213> ORGANISM: Artificial
<220> FEATURE:
<223> OTHER INFORMATION: microRNA mb08-e11

<400> SEQUENCE: 16
agatagctga aggtgactcg gg                                           22

<210> SEQ ID NO 17
<211> LENGTH: 20
<212> TYPE: DNA
<213> ORGANISM: Artificial
<220> FEATURE:
<223> OTHER INFORMATION: mb08-g02

<400> SEQUENCE: 17
aaaatccaaa aactgaatcg                                              20

<210> SEQ ID NO 18
<211> LENGTH: 21
<212> TYPE: DNA
<213> ORGANISM: Artificial
<220> FEATURE:
<223> OTHER INFORMATION: microRNA mb08-h02

<400> SEQUENCE: 18
aatcatctcc aaggagacat c                                            21

<210> SEQ ID NO 19
<211> LENGTH: 20
<212> TYPE: DNA
<213> ORGANISM: Artificial
<220> FEATURE:
<223> OTHER INFORMATION: microRNA mb09-h05

<400> SEQUENCE: 19
gctttaaatc gggatgaaac                                              20

<210> SEQ ID NO 20
<211> LENGTH: 21
<212> TYPE: DNA
<213> ORGANISM: Artificial
<220> FEATURE:
<223> OTHER INFORMATION: microRNA mb10-b02
```

-continued

```
<400> SEQUENCE: 20
aaatctcgat catcaaaccg t                                              21

<210> SEQ ID NO 21
<211> LENGTH: 22
<212> TYPE: DNA
<213> ORGANISM: Artificial
<220> FEATURE:
<223> OTHER INFORMATION: microRNA mb10-d05

<400> SEQUENCE: 21
gggctccgat gaaattgaat tg                                             22

<210> SEQ ID NO 22
<211> LENGTH: 20
<212> TYPE: DNA
<213> ORGANISM: Artificial
<220> FEATURE:
<223> OTHER INFORMATION: microRNA mb10-g05

<400> SEQUENCE: 22
tcggtggatc ttagaaaatt                                                20

<210> SEQ ID NO 23
<211> LENGTH: 22
<212> TYPE: DNA
<213> ORGANISM: Artificial
<220> FEATURE:
<223> OTHER INFORMATION: microRNA mb11-c05

<400> SEQUENCE: 23
tttagccact tacgaggatc tc                                             22

<210> SEQ ID NO 24
<211> LENGTH: 22
<212> TYPE: DNA
<213> ORGANISM: Artificial
<220> FEATURE:
<223> OTHER INFORMATION: microRNA mb11-d04

<400> SEQUENCE: 24
gatgaggaag aggatgagga ag                                             22

<210> SEQ ID NO 25
<211> LENGTH: 21
<212> TYPE: DNA
<213> ORGANISM: Artificial
<220> FEATURE:
<223> OTHER INFORMATION: microRNA mb11-e04

<400> SEQUENCE: 25
catccggtca gcatcatcag t                                              21

<210> SEQ ID NO 26
<211> LENGTH: 21
<212> TYPE: DNA
<213> ORGANISM: Artificial
<220> FEATURE:
<223> OTHER INFORMATION: microRNA mb13-c11

<400> SEQUENCE: 26
ttgtgattgt ggggaaggat g                                              21

<210> SEQ ID NO 27
<211> LENGTH: 21
<212> TYPE: DNA
```

<213> ORGANISM: Artificial
<220> FEATURE:
<223> OTHER INFORMATION: microRNA mb14-a09

<400> SEQUENCE: 27
agacggtttt ctaaaagctt g            21

<210> SEQ ID NO 28
<211> LENGTH: 21
<212> TYPE: DNA
<213> ORGANISM: Artificial
<220> FEATURE:
<223> OTHER INFORMATION: microRNA mb15-a06

<400> SEQUENCE: 28
ctggtttagt cactttcact g            21

<210> SEQ ID NO 29
<211> LENGTH: 20
<212> TYPE: DNA
<213> ORGANISM: Artificial
<220> FEATURE:
<223> OTHER INFORMATION: microRNA mb16-g11

<400> SEQUENCE: 29
cgattccccg cacctccacc              20

<210> SEQ ID NO 30
<211> LENGTH: 22
<212> TYPE: DNA
<213> ORGANISM: Artificial
<220> FEATURE:
<223> OTHER INFORMATION: microRNA mb17-e10

<400> SEQUENCE: 30
ccagttcgcc cgtagtgtgc cc           22

<210> SEQ ID NO 31
<211> LENGTH: 20
<212> TYPE: DNA
<213> ORGANISM: Artificial
<220> FEATURE:
<223> OTHER INFORMATION: microRNA mb18-b02

<400> SEQUENCE: 31
gagaaatgga agatatcgtg              20

<210> SEQ ID NO 32
<211> LENGTH: 22
<212> TYPE: DNA
<213> ORGANISM: Artificial
<220> FEATURE:
<223> OTHER INFORMATION: microRNA mb18-e02

<400> SEQUENCE: 32
tacctggttc gatcctgcca gt           22

<210> SEQ ID NO 33
<211> LENGTH: 22
<212> TYPE: DNA
<213> ORGANISM: Artificial
<220> FEATURE:
<223> OTHER INFORMATION: microRNA mb18-h12

<400> SEQUENCE: 33
gtttcaagcg tcactcgaac cg           22

```
<210> SEQ ID NO 34
<211> LENGTH: 21
<212> TYPE: DNA
<213> ORGANISM: Artificial
<220> FEATURE:
<223> OTHER INFORMATION: microRNA mb19-d08

<400> SEQUENCE: 34
gtggagatcg tggagaagcg g                                              21

<210> SEQ ID NO 35
<211> LENGTH: 22
<212> TYPE: DNA
<213> ORGANISM: Artificial
<220> FEATURE:
<223> OTHER INFORMATION: microRNA mb19-g05

<400> SEQUENCE: 35
aagggaaagc gagaaaaggg ag                                             22

<210> SEQ ID NO 36
<211> LENGTH: 21
<212> TYPE: DNA
<213> ORGANISM: Artificial
<220> FEATURE:
<223> OTHER INFORMATION: microRNA mb20-c07

<400> SEQUENCE: 36
ttgaattgaa gtgcttgaat t                                              21

<210> SEQ ID NO 37
<211> LENGTH: 958
<212> TYPE: DNA
<213> ORGANISM: Artificial
<220> FEATURE:
<223> OTHER INFORMATION: chimeric gene encoding pre-miRNA targeting
      PARP
<220> FEATURE:
<221> NAME/KEY: misc_feature
<222> LOCATION: (1)..(531)
<223> OTHER INFORMATION: CaMV 35S promoter (P35S2)
<220> FEATURE:
<221> NAME/KEY: misc_feature
<222> LOCATION: (532)..(591)
<223> OTHER INFORMATION: untranslated leader sequence (Cab221)
<220> FEATURE:
<221> NAME/KEY: misc_feature
<222> LOCATION: (592)..(736)
<223> OTHER INFORMATION: pre miRNA
<220> FEATURE:
<221> NAME/KEY: variation
<222> LOCATION: (619)..(619)
<223> OTHER INFORMATION: G to A in miPARP2m
<220> FEATURE:
<221> NAME/KEY: variation
<222> LOCATION: (619)..(619)
<223> OTHER INFORMATION: G to A in miRPARP3m
<220> FEATURE:
<221> NAME/KEY: variation
<222> LOCATION: (620)..(620)
<223> OTHER INFORMATION: T to G in miRPARP3m
<220> FEATURE:
<221> NAME/KEY: variation
<222> LOCATION: (630)..(630)
<223> OTHER INFORMATION: G to A in miPARP2m
<220> FEATURE:
<221> NAME/KEY: variation
<222> LOCATION: (630)..(630)
<223> OTHER INFORMATION: G to A in miRPARP3m
<220> FEATURE:
<221> NAME/KEY: misc_feature
<222> LOCATION: (689)..(709)
<223> OTHER INFORMATION: miPARP
```

```
<220> FEATURE:
<221> NAME/KEY: variation
<222> LOCATION: (696)..(696)
<223> OTHER INFORMATION: C to T in miPARP2m
<220> FEATURE:
<221> NAME/KEY: variation
<222> LOCATION: (696)..(696)
<223> OTHER INFORMATION: C to T in miRPARP3m
<220> FEATURE:
<221> NAME/KEY: variation
<222> LOCATION: (706)..(706)
<223> OTHER INFORMATION: A to C in miRPARP3m
<220> FEATURE:
<221> NAME/KEY: variation
<222> LOCATION: (707)..(707)
<223> OTHER INFORMATION: C to T in miPARP2m
<220> FEATURE:
<221> NAME/KEY: variation
<222> LOCATION: (707)..(707)
<223> OTHER INFORMATION: C to T in miRPARP3m
<220> FEATURE:
<221> NAME/KEY: misc_feature
<222> LOCATION: (737)..(958)
<223> OTHER INFORMATION: untranslated leader from the CaMV 35S
      transcript (3' 35S)

<400> SEQUENCE: 37
catggagtca aaaattcaga tcgaggatct aacagaactc gccgtgaaga ctggcgaaca      60
gttcatacag agtcttttac gactcaatga caagaagaaa atcttcgtca acatggtgga     120
gcacgacact ctcgtctact ccaagaatat caaagataca gtctcagaag accaaagggc     180
tattgagact tttcaacaaa gggtaatatc gggaaacctc ctcggattcc attgcccagc     240
tatctgtcac ttcatcaaaa ggacagtaga aaaggaaggt ggcacctaca aatgccatca     300
ttgcgataaa ggaaaggcta tcgttcaaga tgcctctgcc gacagtggtc ccaaagatgg     360 accccccaccc acgaggagca tcgtggaaaa agaagacgtt ccaaccacgt cttcaaagca     420
agtggattga tgtgatatct ccactgacgt aagggatgac gcacaatccc actatccttc     480
gcaagaccct tcctctatat aaggaagttc atttcatttg gagaggactc gagctcattt     540
ctctattact tcagccataa caaaagaact cttttctctt cttattaaac caaaaccatg     600
gatgagagag tcccttttgg ttacatcttt ggaacaggga tcttacctga ccacacacgt     660
agatatacat tattctctct agattatccc ttttccaaac atgtaaccat cagtactctc     720
tcgtgctagc aagcttggac acgctgaaat caccagtctc tctctacaaa tctatctctc     780
tctattttct ccataataat gtgtgagtag ttcccagata agggaattag ggttcctata     840
gggtttcgct catgtgttga gcatataaga aacccttagt atgtatttgt atttgtaaaa     900
tacttctatc aataaaattt ctaattccta aaaccaaaat ccagtactaa aatccaga      958

<210> SEQ ID NO 38
<211> LENGTH: 21
<212> TYPE: DNA
<213> ORGANISM: Artificial
<220> FEATURE:
<223> OTHER INFORMATION: microRNA miRPARP7

<400> SEQUENCE: 38
tagacgatat atacattgta c                                                21

<210> SEQ ID NO 39
<211> LENGTH: 148
<212> TYPE: DNA
<213> ORGANISM: Artificial
<220> FEATURE:
<223> OTHER INFORMATION: pre-microRNA398a
<220> FEATURE:
```

```
<221> NAME/KEY: misc_feature
<222> LOCATION: (34)..(54)
<223> OTHER INFORMATION: miR398a*
<220> FEATURE:
<221> NAME/KEY: misc_feature
<222> LOCATION: (98)..(118)
<223> OTHER INFORMATION: miR398a

<400> SEQUENCE: 39
gtctccatgg gaacaacagg aggtgaaatt tcaaaggagt ggcatgtgaa cacatatcct      60
atggtttctt caaatttcca ttgaaaccat tgagttttgt gttctcaggt caccccttg     120 aatctcccct gttccattgc tagctctg                                        148

<210> SEQ ID NO 40
<211> LENGTH: 148
<212> TYPE: DNA
<213> ORGANISM: Artificial
<220> FEATURE:
<223> OTHER INFORMATION: pre-microRNAPARP7
<220> FEATURE:
<221> NAME/KEY: misc_feature
<222> LOCATION: (34)..(54)
<223> OTHER INFORMATION: miRPARP7*
<220> FEATURE:
<221> NAME/KEY: misc_feature
<222> LOCATION: (98)..(118)
<223> OTHER INFORMATION: miRPARP7

<400> SEQUENCE: 40
gtctccatgg gaacaacagg aggtgaaatt tcagtactat gtaaatttcg tctatatcct      60
atggtttctt caaatttcca ttgaaaccat tgagttttag acgatatata cattgtactg     120
aatctcccct gttccattgc tagctctg                                        148

<210> SEQ ID NO 41
<211> LENGTH: 21
<212> TYPE: DNA
<213> ORGANISM: Artificial
<220> FEATURE:
<223> OTHER INFORMATION: microRNA miRPARP2-8

<400> SEQUENCE: 41
tctcataata gcttcctcgc g                                                21

<210> SEQ ID NO 42
<211> LENGTH: 148
<212> TYPE: DNA
<213> ORGANISM: Artificial
<220> FEATURE:
<223> OTHER INFORMATION: pre-microRNA miRPARP2-8
<220> FEATURE:
<221> NAME/KEY: misc_feature
<222> LOCATION: (34)..(54)
<223> OTHER INFORMATION: miRPARP2-8*
<220> FEATURE:
<221> NAME/KEY: misc_feature
<222> LOCATION: (98)..(118)
<223> OTHER INFORMATION: miRPARP2-8

<400> SEQUENCE: 42
gtctccatgg gaacaacagg aggtgaaatt tcacgcgtgg aagataatat gagatatcct      60
atggtttctt caaatttcca ttgaaaccat tgagttttct cataatagct tcctcgcgtg     120
aatctcccct gttccattgc tagctctg                                        148

<210> SEQ ID NO 43
<211> LENGTH: 62
<212> TYPE: RNA
```

```
<213> ORGANISM: Artificial Sequence
<220> FEATURE:
<223> OTHER INFORMATION: Chemically Synthesized

<400> SEQUENCE: 43
augagagagu cccuuugaua uuggccuggu ucacucagau cuuaccugac cacacacgua    60
ga                                                                   62

<210> SEQ ID NO 44
<211> LENGTH: 61
<212> TYPE: RNA
<213> ORGANISM: Artifical Sequence
<220> FEATURE:
<223> OTHER INFORMATION: Chemically Synthesized

<400> SEQUENCE: 44
ugcucucuca ugacucuaua accgcgccga guuagucuau uagaucucuc uuauuacaua    60
u                                                                    61

<210> SEQ ID NO 45
<211> LENGTH: 62
<212> TYPE: RNA
<213> ORGANISM: Artificial Sequence
<220> FEATURE:
<223> OTHER INFORMATION: Chemically Synthesized

<400> SEQUENCE: 45
augagagagu cccuuuuggu uacauguuug gaaaagggau cuuaccugac cacacacgua    60
ga                                                                   62

<210> SEQ ID NO 46
<211> LENGTH: 61
<212> TYPE: RNA
<213> ORGANISM: Artificial Sequence
<220> FEATURE:
<223> OTHER INFORMATION: Chemically Synthesized

<400> SEQUENCE: 46
ugcucucuca ugacuaccaa uguacaaacc uuuucccuau uagaucucuc uuauuacaua    60
u                                                                    61

<210> SEQ ID NO 47
<211> LENGTH: 62
<212> TYPE: RNA
<213> ORGANISM: Artificial Sequence
<220> FEATURE:
<223> OTHER INFORMATION: Chemically Synthesized

<400> SEQUENCE: 47
augagagagu cccuuuuggu uacaucuuug gaacagggau cuuaccugac cacacacgua    60
ga                                                                   62

<210> SEQ ID NO 48
<211> LENGTH: 61
<212> TYPE: RNA
<213> ORGANISM: Artificial Sequence
<220> FEATURE:
<223> OTHER INFORMATION: Chemically Synthesized

<400> SEQUENCE: 48
ugcucucuca ugacuaccaa uguacaaacc uuuucccuau uagaucucuc uuauuacaua    60
u                                                                    61
```

<210> SEQ ID NO 49
<211> LENGTH: 21
<212> TYPE: RNA
<213> ORGANISM: Artifical Sequence
<220> FEATURE:
<223> OTHER INFORMATION: Parp1

<400> SEQUENCE: 49
ugguuacaug uuuggaaaag g                                              21

<210> SEQ ID NO 50
<211> LENGTH: 21
<212> TYPE: RNA
<213> ORGANISM: Artificial Sequence
<220> FEATURE:
<223> OTHER INFORMATION: miRPARP

<400> SEQUENCE: 50
accaauguac aaaccuuuuc c                                              21

<210> SEQ ID NO 51
<211> LENGTH: 21
<212> TYPE: RNA
<213> ORGANISM: Artificial Sequence
<220> FEATURE:
<223> OTHER INFORMATION: miRPARP2m

<400> SEQUENCE: 51
acuaauguac aaaucuuuuc c                                              21

<210> SEQ ID NO 52
<211> LENGTH: 21
<212> TYPE: RNA
<213> ORGANISM: Artificial Sequence
<220> FEATURE:
<223> OTHER INFORMATION: miRPARP3m

<400> SEQUENCE: 52
acucauguac aaaucuuuuc c                                              21

<210> SEQ ID NO 53
<211> LENGTH: 21
<212> TYPE: DNA
<213> ORGANISM: Artificial Sequence
<220> FEATURE:
<223> OTHER INFORMATION: AtPARP1

<400> SEQUENCE: 53
gtacaatgag tatatcgtct a                                              21

<210> SEQ ID NO 54
<211> LENGTH: 22
<212> TYPE: DNA
<213> ORGANISM: Artificial Sequence
<220> FEATURE:
<223> OTHER INFORMATION: AtPARP2

<400> SEQUENCE: 54
gtacaactga atatatagtc ta                                             22

<210> SEQ ID NO 55
<211> LENGTH: 21
<212> TYPE: DNA
<213> ORGANISM: Artificial Sequence
<220> FEATURE:
<223> OTHER INFORMATION: miRPARP7

```
<400> SEQUENCE: 55
catgttacat atatagcaga t                                              21

<210> SEQ ID NO 56
<211> LENGTH: 22
<212> TYPE: DNA
<213> ORGANISM: Artificial Sequence
<220> FEATURE:
<223> OTHER INFORMATION: AtPARP1

<400> SEQUENCE: 56
catcagctga gtrtgcggga aa                                             22

<210> SEQ ID NO 57
<211> LENGTH: 21
<212> TYPE: DNA
<213> ORGANISM: Artificial Sequence
<220> FEATURE:
<223> OTHER INFORMATION: AtPARP2

<400> SEQUENCE: 57
cgtgaggaag ctattaagag a                                              21

<210> SEQ ID NO 58
<211> LENGTH: 21
<212> TYPE: DNA
<213> ORGANISM: Artificial Sequence
<220> FEATURE:
<223> OTHER INFORMATION: miRPARP8

<400> SEQUENCE: 58
gcgctccttc gataatactc t                                              21

<210> SEQ ID NO 59
<211> LENGTH: 16
<212> TYPE: PRT
<213> ORGANISM: Artificial Sequence
<220> FEATURE:
<223> OTHER INFORMATION: Chemically Synthezied
<220> FEATURE:
<221> NAME/KEY: misc_feature
<222> LOCATION: (3)..(6)
<223> OTHER INFORMATION: Xaa can be any amino acid
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (10)..(14)
<223> OTHER INFORMATION: Xaa can be any amino acid

<400> SEQUENCE: 59

Arg Gly Xaa Xaa Xaa Xaa Gly Xaa Lys Xaa Xaa Xaa Xaa Xaa Arg Leu
1               5                   10                  15

<210> SEQ ID NO 60
<211> LENGTH: 33
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(1)
<223> OTHER INFORMATION: Xaa can be any amino acid
<220> FEATURE:
<221> NAME/KEY: misc_feature
<222> LOCATION: (3)..(3)
<223> OTHER INFORMATION: Xaa can be any amino acid
```

```
<220> FEATURE:
<221> NAME/KEY: misc_feature
<222> LOCATION: (5)..(7)
<223> OTHER INFORMATION: Xaa can be any amino acid
<220> FEATURE:
<221> NAME/KEY: misc_feature
<222> LOCATION: (9)..(10)
<223> OTHER INFORMATION: Xaa can be any amino acid
<220> FEATURE:
<221> NAME/KEY: misc_feature
<222> LOCATION: (12)..(13)
<223> OTHER INFORMATION: Xaa can be any amino acid
<220> FEATURE:
<221> NAME/KEY: misc_feature
<222> LOCATION: (17)..(19)
<223> OTHER INFORMATION: Xaa can be any amino acid
<220> FEATURE:
<221> NAME/KEY: misc_feature
<222> LOCATION: (23)..(24)
<223> OTHER INFORMATION: Xaa can be any amino acid
<220> FEATURE:
<221> NAME/KEY: misc_feature
<222> LOCATION: (27)..(27)
<223> OTHER INFORMATION: Xaa can be any amino acid
<220> FEATURE:
<221> NAME/KEY: misc_feature
<222> LOCATION: (30)..(31)
<223> OTHER INFORMATION: Xaa can be any amino acid

<400> SEQUENCE: 60

Xaa Leu Xaa Val Xaa Xaa Xaa Arg Xaa Xaa Leu Xaa Xaa Arg Gly Leu
1               5                   10                  15

Xaa Xaa Xaa Gly Val Lys Xaa Xaa Leu Val Xaa Arg Leu Xaa Xaa Ala
            20                  25                  30

Ile

<210> SEQ ID NO 61
<211> LENGTH: 30
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (3)..(5)
<223> OTHER INFORMATION: Xaa can be any amino acid
<220> FEATURE:
<221> NAME/KEY: misc_feature
<222> LOCATION: (8)..(10)
<223> OTHER INFORMATION: Xaa can be any amino acid
<220> FEATURE:
<221> NAME/KEY: misc_feature
<222> LOCATION: (12)..(13)
<223> OTHER INFORMATION: Xaa can be any amino acid
<220> FEATURE:
<221> NAME/KEY: misc_feature
<222> LOCATION: (16)..(19)
<223> OTHER INFORMATION: Xaa can be any amino acid
<220> FEATURE:
<221> NAME/KEY: misc_feature
<222> LOCATION: (21)..(21)
<223> OTHER INFORMATION: Xaa can be any amino acid
<220> FEATURE:
<221> NAME/KEY: misc_feature
<222> LOCATION: (25)..(26)
<223> OTHER INFORMATION: Xaa can be any amino acid
<220> FEATURE:
<221> NAME/KEY: misc_feature
<222> LOCATION: (29)..(30)
<223> OTHER INFORMATION: Xaa can be any amino acid

<400> SEQUENCE: 61

Gly Met Xaa Xaa Xaa Glu Leu Xaa Xaa Xaa Ala Xaa Xaa Arg Gly Xaa
1               5                   10                  15
```

-continued

Xaa Xaa Xaa Gly Xaa Lys Lys Asp Xaa Xaa Arg Leu Xaa Xaa
            20                  25                  30

<210> SEQ ID NO 62
<211> LENGTH: 13
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (8)..(10)
<223> OTHER INFORMATION: Xaa can be any amino acid

<400> SEQUENCE: 62

Leu Xaa Val Asp Phe Ala Asn Xaa Xaa Xaa Gly Gly Gly
1               5                   10

<210> SEQ ID NO 63
<211> LENGTH: 26
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (8)..(10)
<223> OTHER INFORMATION: Xaa can be any amino acid
<220> FEATURE:
<221> NAME/KEY: misc_feature
<222> LOCATION: (14)..(17)
<223> OTHER INFORMATION: Xaa can be any amino acid
<220> FEATURE:
<221> NAME/KEY: misc_feature
<222> LOCATION: (19)..(19)
<223> OTHER INFORMATION: Xaa can be any amino acid

<400> SEQUENCE: 63

Leu Xaa Val Asp Phe Ala Asn Xaa Xaa Xaa Gly Gly Gly Xaa Xaa Xaa
1               5                   10                  15

Xaa Gly Xaa Val Gln Glu Glu Ile Arg Phe
            20                  25

<210> SEQ ID NO 64
<211> LENGTH: 31
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (8)..(10)
<223> OTHER INFORMATION: Xaa can be any amino acid
<220> FEATURE:
<221> NAME/KEY: misc_feature
<222> LOCATION: (14)..(17)
<223> OTHER INFORMATION: Xaa can be any amino acid
<220> FEATURE:
<221> NAME/KEY: misc_feature
<222> LOCATION: (19)..(19)
<223> OTHER INFORMATION: Xaa can be any amino acid
<220> FEATURE:

```
<221> NAME/KEY: misc_feature
<222> LOCATION: (27)..(29)
<223> OTHER INFORMATION: Xaa can be any amino acid

<400> SEQUENCE: 64

Leu Xaa Val Asp Phe Ala Asn Xaa Xaa Xaa Gly Gly Gly Xaa Xaa Xaa
1               5                   10                  15

Xaa Gly Xaa Val Gln Glu Glu Ile Arg Phe Xaa Xaa Xaa Pro Glu
            20                  25                  30

<210> SEQ ID NO 65
<211> LENGTH: 12
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (10)..(10)
<223> OTHER INFORMATION: Xaa can be any amino acid

<400> SEQUENCE: 65

Thr Gly Xaa Trp Gly Cys Gly Xaa Phe Xaa Gly Asp
1               5                   10

<210> SEQ ID NO 66
<211> LENGTH: 20
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
<222> LOCATION: (10)..(10)
<223> OTHER INFORMATION: Xaa can be any amino acid
<220> FEATURE:
<221> NAME/KEY: misc_feature
<222> LOCATION: (13)..(14)
<223> OTHER INFORMATION: Xaa can be any amino acid
<220> FEATURE:
<221> NAME/KEY: misc_feature
<222> LOCATION: (17)..(19)
<223> OTHER INFORMATION: Xaa can be any amino acid

<400> SEQUENCE: 66

Thr Gly Xaa Trp Gly Cys Gly Ala Phe Xaa Gly Asp Xaa Xaa Leu Lys
1               5                   10                  15

Xaa Xaa Xaa Gln
            20

<210> SEQ ID NO 67
<211> LENGTH: 13
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (2)..(4)
<223> OTHER INFORMATION: Xaa can be any amino acid
```

```
<220> FEATURE:
<221> NAME/KEY: misc_feature
<222> LOCATION: (6)..(9)
<223> OTHER INFORMATION: Xaa can be any amino acid

<400> SEQUENCE: 67

Asp Xaa Xaa Xaa Arg Xaa Xaa Xaa Xaa Ala Ile Asp Ala
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (3)..(4)
<223> OTHER INFORMATION: Xaa can be any amino acid
<220> FEATURE:
<221> NAME/KEY: misc_feature
<222> LOCATION: (7)..(8)
<223> OTHER INFORMATION: Xaa can be any amino acid

<400> SEQUENCE: 68

Arg Glu Xaa Xaa Lys Ala Xaa Xaa Gly Phe
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (2)..(5)
<223> OTHER INFORMATION: Xaa can be any amino acid
<220> FEATURE:
<221> NAME/KEY: misc_feature
<222> LOCATION: (7)..(7)
<223> OTHER INFORMATION: Xaa can be any amino acid

<400> SEQUENCE: 69

Gly Xaa Xaa Xaa Xaa Ser Xaa Tyr Thr Gly Tyr
1               5                   10
```